(12) United States Patent
Rathi

(10) Patent No.: US 12,087,440 B1
(45) Date of Patent: Sep. 10, 2024

(54) METHODS AND APPARATUS FOR UTILIZING AN AUTONOMOUS VEHICLE TO SUPPORT CONTACTLESS MEDICAL INTERACTIONS

(71) Applicant: Nuro, Inc., Mountain View, CA (US)

(72) Inventor: Benjamin Bhanu Rathi, Novi, MI (US)

(73) Assignee: NURO, INC., Mountain View, CA (US)

( * ) Notice: Subject to any disclaimer, the term of this patent is extended or adjusted under 35 U.S.C. 154(b) by 88 days.

(21) Appl. No.: 17/201,366

(22) Filed: Mar. 15, 2021

Related U.S. Application Data

(60) Provisional application No. 63/006,067, filed on Apr. 6, 2020.

(51) Int. Cl.
| | | |
|---|---|---|
| *G16H 40/67* | (2018.01) | |
| *G05D 1/00* | (2024.01) | |
| *G16H 50/20* | (2018.01) | |
| *G16H 80/00* | (2018.01) | |

(52) U.S. Cl.
CPC ........... *G16H 40/67* (2018.01); *G05D 1/0011* (2013.01); *G16H 50/20* (2018.01); *G16H 80/00* (2018.01)

(58) Field of Classification Search
USPC .............................................................. 705/2
See application file for complete search history.

(56) References Cited

U.S. PATENT DOCUMENTS

| | | | |
|---|---|---|---|
| 11,323,196 B1 * | 5/2022 | Newton ................ | H04J 3/1682 |
| 2018/0080188 A1 | 3/2018 | Pickover et al. | |
| 2019/0091738 A1 | 3/2019 | Chen | |
| 2019/0308612 A1 * | 10/2019 | Lavoie .................. | G05D 1/028 |
| 2019/0392295 A1 | 11/2019 | Kanitz | |
| 2020/0098461 A1 * | 3/2020 | Macoviak ............ | G06Q 30/018 |
| 2020/0411170 A1 * | 12/2020 | Brown .................... | G06N 20/00 |
| 2021/0125722 A1 * | 4/2021 | Sherkat ................ | G06V 10/764 |
| 2023/0078951 A1 * | 3/2023 | Kadri ..................... | G16H 10/20 |
| | | | 705/2 |

FOREIGN PATENT DOCUMENTS

CN              107651049 A     2/2018

OTHER PUBLICATIONS

Von Urff, C. A. (2004). Facilitating delivery of advanced telemedicine services to rural areas and lesser developed countries through a new hybrid telecommunications system . . . performance criteria (Order No. 3278157). Available from ProQuest Dissertations and Theses Professional (Year: 2004).*
International Preliminary Report on Patentability for PCT application PCT/US2021/02247.

\* cited by examiner

*Primary Examiner* — Christopher L Gilligan
*Assistant Examiner* — Bennett Stephen Erickson
(74) *Attorney, Agent, or Firm* — Edell, Shapiro & Finnan, LLC

(57) ABSTRACT

According to one aspect, a vehicle includes a chassis and a system configured to cause the vehicle to operate autonomously and carried on the chassis. The vehicle also includes a first compartment carried on the chassis, the first compartment having a first mechanism contained therein and configured to facilitate performing a first procedure. A second mechanism carried on the chassis is also included in the vehicle. The second mechanism is configured to support a telepresence session. In one embodiment, the first procedure is a first medical procedure, and first mechanism is configured to be remotely controlled to perform the first medical procedure.

11 Claims, 15 Drawing Sheets

METHODS AND APPARATUS FOR UTILIZING AN AUTONOMOUS VEHICLE TO SUPPORT CONTACTLESS MEDICAL INTERACTIONS

PRIORITY CLAIM

This patent application claims the benefit of priority under 35 U.S.C. § 119 to U.S. Provisional Patent Application No. 63/006,067, filed Apr. 6, 2020 and entitled "METHODS AND APPARATUS FOR UTILIZING AN AUTONOMOUS VEHICLE WHEN A SHELTER-IN-PLACE ORDER IS IN EFFECT," which is incorporated herein by reference in its entirety.

TECHNICAL FIELD

The disclosure relates to the use of autonomous vehicles. More particularly, the disclosure relates to deploying autonomous delivery vehicles to support needs of society when a shelter-in-place order for biological threats is in effect.

BACKGROUND

In some situations, it may not be practical, desirable, or possible for individuals to leave their homes to acquire necessary items, and/or to visit medical offices or hospitals to seek medical attention. For example, during a crisis such as a global pandemic, when shelter-in-place or stay-at-home orders are in effect, individuals may not be able to or willing to leave their homes to procure goods and/or to receive medical attention.

The ability to receive medical attention without having to visit a medical office or hospital would allow individuals to avoid crowded medical offices and hospitals while still receiving medical attention. Further, the ability to receive medical treatment or to undergo medical procedures without having to visit a medical office or hospital would enable individuals to avoid potentially crowded locations and, hence, reduce the likelihood that the individuals may contract an illness.

BRIEF DESCRIPTION OF THE DRAWINGS

The disclosure will be readily understood by the following detailed description in conjunction with the accompanying drawings in which.

DESCRIPTION OF EXAMPLE EMBODIMENTS

General Overview

Figure 1:
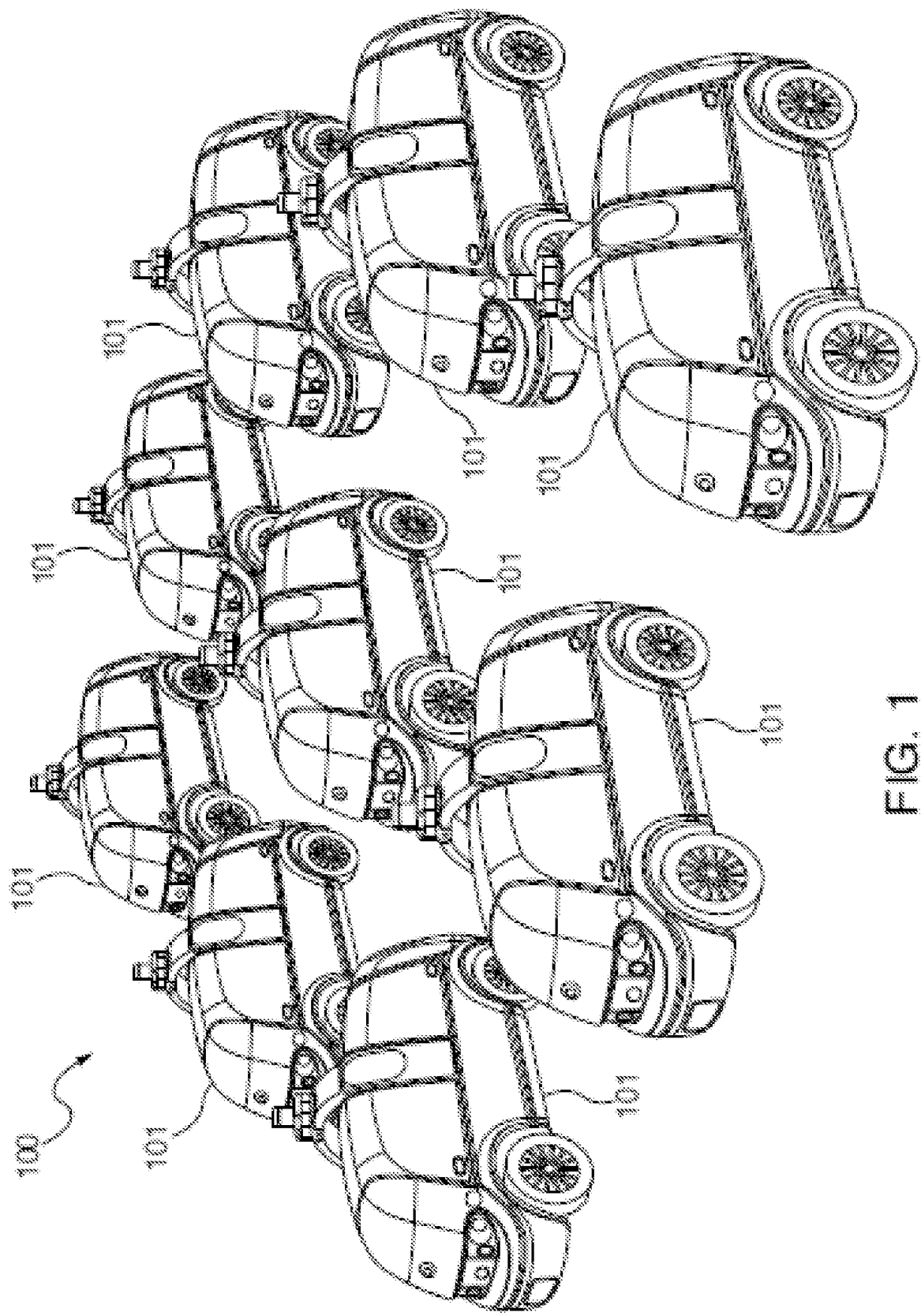
FIG. 1 is a diagrammatic representation of an autonomous vehicle fleet in accordance with an embodiment.

An autonomous delivery vehicle may be deployed to facilitate deliveries and to provide medical-related services, e.g., when it is not advisable or impossible for individuals to leave their places of residence. An autonomous vehicle deployed to provide medical-related services may disinfect or otherwise clean items used for such services. For example, an autonomous vehicle may carry medical-related goods, e.g., medical tests kits, as well as apparatuses that allow for medical procedures to be facilitated or otherwise performed using components installed on the delivery vehicle.

According to one aspect, a vehicle includes a chassis and a system configured to cause the vehicle to operate autonomously and carried on the chassis. The vehicle also includes a first compartment carried on the chassis, the first compartment having a first mechanism contained therein and configured to facilitate performing a first procedure. A second mechanism carried on the chassis is also included in the vehicle. The second mechanism is configured to support a telepresence session such as a telemedicine session. In one embodiment, the first mechanism is configured to be remotely controlled to perform the first procedure which is a first medical procedure.

According to another aspect, a method includes autonomously driving an autonomous vehicle to a destination, the destination being associated with a service recipient, the autonomous vehicle including at least a first compartment, the first compartment having a first mechanism contained therein, the first mechanism configured to facilitate a first procedure. The method also includes verifying whether the service recipient is allowed to access the first compartment, and at least temporarily preventing the service recipient from accessing the first compartment when it is not verified that the service recipient is allowed to access the first compartment. When it is verified that the service recipient is allowed to access the first compartment, the service is provided with access to the first compartment, wherein providing the service recipient with access to the first compartment includes performing the first procedure on the service recipient using the first mechanism. In one embodiment, the first procedure is a first medical procedure and the service recipient is a patient.

In accordance with still another aspect, a vehicle includes a chassis, a first system, a telepresence system, a first mechanism, and a communications system. The first system is carried on the chassis, and configured to enable autonomous operation of the vehicle. The telepresence system is carried on the chassis, and configured to support a telepresence session such as a telemedicine session. The first mechanism carried on the chassis, and configured to perform a procedure on a service recipient, e.g., a patient. The communications system is carried on the chassis, and is arranged to enable the telepresence system to communicate with a remote telepresence endpoint during the telepresence session. In one embodiment, the vehicle also includes at least one compartment and a sanitizing arrangement, the sanitizing arrangement included in the at least one compartment and configured to sanitize the first mechanism.

DESCRIPTION

Situations may arise in which autonomous delivery vehicles may be leveraged to not only deliver goods, but to provide services or support for services such as medical services. For example, during a pandemic in which individuals are expected to shelter-in-place or to stay at home to avoid the spread of illness or disease, autonomous delivery vehicles delivery vehicles may also be used to provide services such as medical testing and vaccination services. When autonomous delivery vehicles are outfitted to provide medical testing services, an individual may effectively take a medical test without having to visit a medical office or a hospital, and thereby avoid physical contact with other individuals. Similarly, when autonomous delivery vehicles are outfitted to administer medication or vaccines, an individual may effectively be medicated or vaccinated without having to visit a medical office or a hospital. Avoiding physical contact with other individuals may allow for adherence to social distancing guidelines, for example, and, thus, slow the spread of illness or disease during a pandemic.

In one embodiment, an autonomous delivery vehicle may carry onboard components that allow the autonomous delivery vehicle to essentially function as a mobile medical clinic. Components may include, but are not limited to including, testing equipment configured to allow a service recipient, e.g., a patient, to be tested for a particular affliction, telecommunications equipment that allows a medical professional to communicate with a patient, teleoperations equipment that may be controlled remotely by a medical professional to perform a procedure on a patient, etc. Compartments in which medical components are carried may be configured to decontaminate, sanitize, disinfect, sterilize, and/or otherwise clean one or both of the compartments and the medical components. It should be appreciated that telecommunications equipment may generally include telepresence equipment.

Autonomous vehicles such as autonomous delivery vehicles configured to support medical purposes may generally operate as part of an overall fleet of vehicles. Referring initially to FIG. 1, an autonomous vehicle fleet will be described in accordance with an embodiment. An autonomous vehicle fleet 100 includes a plurality of autonomous vehicles 101, or robot vehicles. Autonomous vehicles 101 are generally arranged to transport and/or to deliver cargo, items, and/or goods. Autonomous vehicles 101 may be fully autonomous and/or semi-autonomous vehicles. In general, each autonomous vehicle 101 may be a vehicle that is capable of travelling in a controlled manner for a period of time without intervention, e.g., without human intervention. As will be discussed in more detail below, each autonomous vehicle 101 may include a power system, a propulsion or conveyance system, a navigation module, a control system or controller, a communications system, a processor, and a sensor system.

Dispatching of autonomous vehicles 101 in autonomous vehicle fleet 100 may be coordinated by a fleet management module (not shown). The fleet management module may dispatch autonomous vehicles 101 for purposes of transporting, delivering, and/or retrieving goods or services in an unstructured open environment or a closed environment. In one embodiment, the fleet management module may dispatch autonomous vehicle 101 to provide medical services in an unstructured open environment or a closed environment.

Figure 2:
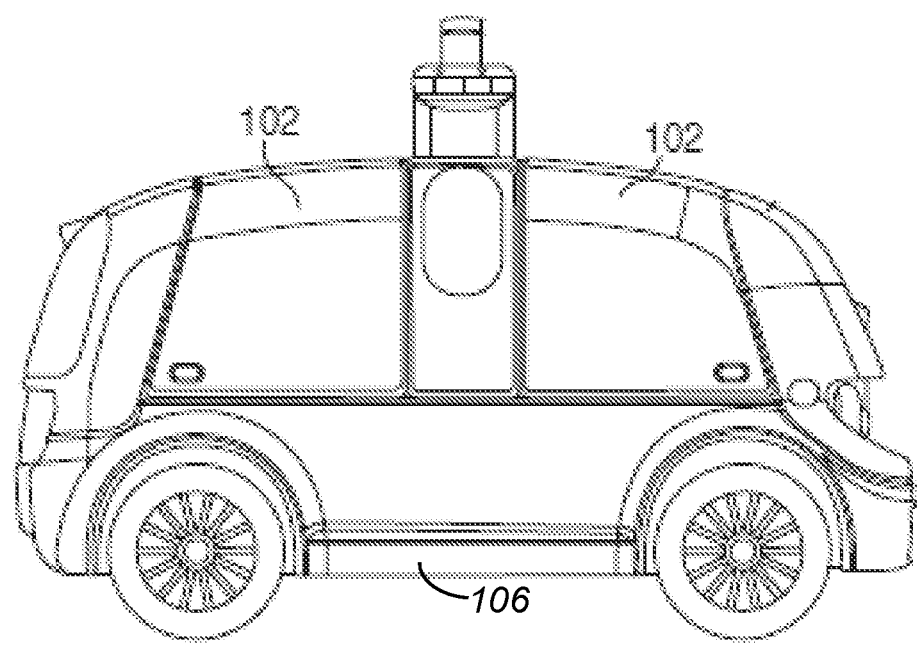
FIG. 2 is a diagrammatic representation of a side of an autonomous vehicle in accordance with an embodiment.

FIG. 2 is a diagrammatic representation of a side of an autonomous vehicle, e.g., one of autonomous vehicles 101 of FIG. 1, in accordance with an embodiment. Autonomous vehicle 101, as shown, is a vehicle configured for land travel. Typically, autonomous vehicle 101 includes physical vehicle components such as a body or a chassis 106, as well as conveyance mechanisms, e.g., wheels. In one embodiment, autonomous vehicle 101 may be relatively narrow, e.g., approximately two to approximately five feet wide, and may have a relatively low mass and relatively low center of gravity for stability. Autonomous vehicle 101 may be arranged to have a working speed or velocity range of between approximately one and approximately forty-five miles per hour (mph), e.g., approximately twenty-five miles per hour. In some embodiments, autonomous vehicle 101 may have a substantially maximum speed or velocity in range between approximately thirty and approximately ninety mph.

Autonomous vehicle 101 includes a plurality of compartments 102. Compartments 102 may be assigned to one or more entities, such as one or more customer, retailers, and/or vendors. Compartments 102 are generally arranged to contain cargo, items, and/or goods, and may be arranged to receive modular inserts (not shown) that allow the interior of compartments 102 to be configured for specific purposes, e.g., configured to support the administering of a medical test. Typically, compartments 102 may be secure compartments. It should be appreciated that the number of compartments 102 may vary. That is, although two compartments 102 are shown, autonomous vehicle 101 is not limited to including two compartments 102. In one embodiment, compartments 102 each include connections (not shown) which provide power and data connections in compartments 102, or to any inserts (not shown) which may be provided with power and/or commands and data.

Figure 3:
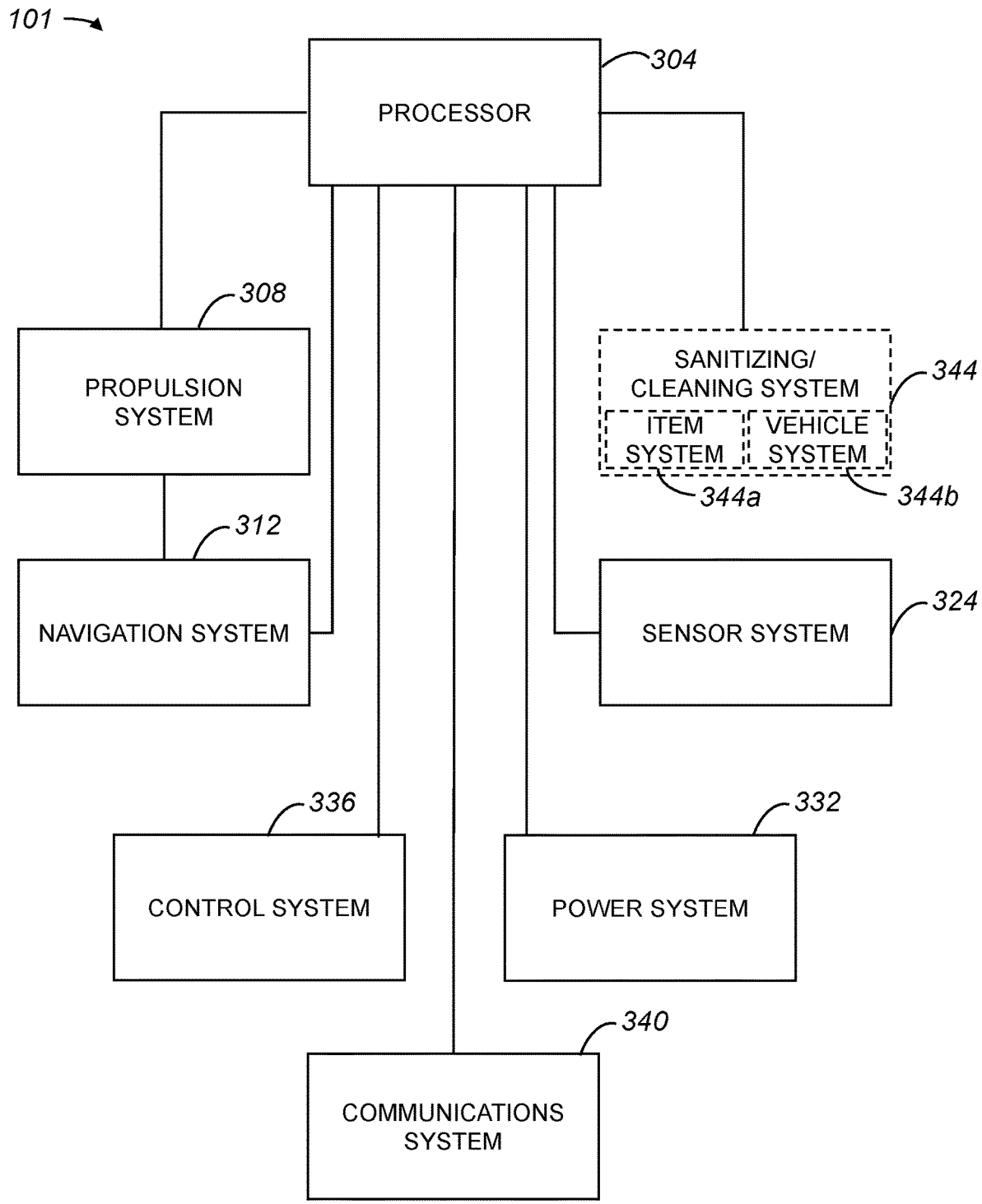
FIG. 3 is a block diagram representation of an autonomous vehicle in accordance with an embodiment.

FIG. 3 is a block diagram representation of an autonomous vehicle, e.g., autonomous vehicle 101 of FIG. 1, in accordance with an embodiment. An autonomous vehicle 101 includes a processor 304, a propulsion system 308, a navigation system 312, a sensor system 324, a power system 332, a control system 336, a communications system 340, and an optional sanitizing/cleaning system 344. It should be appreciated that processor 304, propulsion system 308, navigation system 312, sensor system 324, power system 332, communications system 340, and optional sanitizing/cleaning system 344 are all coupled to a chassis or body of autonomous vehicle 101.

Processor 304 is arranged to send instructions to and to receive instructions from or for various components such as propulsion system 308, navigation system 312, sensor system 324, power system 332, and control system 336. Propulsion system 308, or a conveyance system, is arranged to cause autonomous vehicle 101 to move, e.g., drive. For example, when autonomous vehicle 101 is configured with a multi-wheeled automotive configuration as well as steering, braking systems and an engine, propulsion system 308 may be arranged to cause the engine, wheels, steering, and braking systems to cooperate to drive. In general, propulsion system 308 may be configured as a drive system with a propulsion engine, wheels, treads, wings, rotors, blowers, rockets, propellers, brakes, etc. The propulsion engine may be a gas engine, a turbine engine, an electric motor, and/or a hybrid gas and electric engine.

Navigation system 312 may control propulsion system 308 to navigate autonomous vehicle 101 through paths and/or within unstructured open or closed environments. Navigation system 312 may include at least one of digital maps, street view photographs, and a global positioning system (GPS) point. Maps, for example, may be utilized in cooperation with sensors included in sensor system 324 to allow navigation system 312 to cause autonomous vehicle 101 to navigate through an environment.

Sensor system 324 includes any sensors, as for example LiDAR, radar, ultrasonic sensors, microphones, altimeters, and/or cameras. Sensor system 324 generally includes onboard sensors which allow autonomous vehicle 101 to safely navigate, and to ascertain when there are objects near autonomous vehicle 101. In one embodiment, sensor system 324 may include propulsion systems sensors that monitor drive mechanism performance, drive train performance, and/or power system levels.

Power system 332 is arranged to provide power to autonomous vehicle 101. Power may be provided as electrical power, gas power, or any other suitable power, e.g., solar power or battery power. In one embodiment, power system 332 may include a main power source, and an auxiliary power source that may serve to power various components of autonomous vehicle 101 and/or to generally provide power to autonomous vehicle 101 when the main power source does not have the capacity to provide sufficient power.

Communications system 340 allows autonomous vehicle 101 to communicate, as for example, wirelessly, with a fleet management system (not shown) that allows autonomous vehicle 101 to be controlled remotely. Communications system 340 generally obtains or receives data, stores the data, and transmits or provides the data to a fleet management system and/or to autonomous vehicles 101 within a fleet 100. The data may include, but is not limited to including, information relating to scheduled requests or orders, information relating to on-demand requests or orders, and/or information relating to a need for autonomous vehicle 101 to reposition itself, e.g., in response to an anticipated demand.

Optional sanitizing/cleaning system 344 is generally arranged to sanitize, disinfect, sterilize, purify, decontaminate, and/or clean vehicle 101, as well as to clean items carried in vehicle 101, e.g., items such as devices which support medical services that are contained within compartments 102 as shown in FIG. 2. It should be appreciated that when cleaning items carried in vehicle 101, optional sanitizing/cleaning system 344 may also clean the interior of compartments 102 and inserts in compartments 102 such as inserts that hold the items. Optional sanitizing/cleaning system 344 may include an item cleaning system 344a and a vehicle cleaning system 344b.

Item cleaning system 344a may be arranged to clean items such as devices which support medical services that are transported in a compartment of vehicle 101. Item cleaning system 344a may be arranged, in one embodiment, to disinfect items that are being delivered to a customer and mechanisms in a compartment of vehicle 101 including, but not limited to including, modular inserts arranged to hold the items, mechanical components arranged to facilitate the loading and/or unloading of the items, etc. Item cleaning system 344a may be arranged to disinfect items using ultraviolet (UV) light, heat, and/or chemicals.

Vehicle cleaning system 344b is arranged to clean vehicle 101, e.g., the exterior surfaces of vehicle 101. In one embodiment, vehicle cleaning system 344b may include a reservoir that holds water or a cleaning fluid, a dispensing mechanism such as a nozzle, and a wiper mechanism. It should be appreciated that vehicle cleaning system 344b may further being arranged to clean interior surfaces of vehicle 101 including, but not limited to including, the interior of a compartment of vehicle 101.

In some embodiments, control system 336 may cooperate with processor 304 to determine where autonomous vehicle 101 may safely travel, and to determine the presence of objects in a vicinity around autonomous vehicle 101 based on data, e.g., results, from sensor system 324. In other words, control system 336 may cooperate with processor 304 to effectively determine what autonomous vehicle 101 may do within its immediate surroundings. Control system 336 in cooperation with processor 304 may essentially control power system 332 and navigation system 312 as part of driving or conveying autonomous vehicle 101. Additionally, control system 336 may cooperate with processor 304 and communications system 340 to provide data to or obtain data from other autonomous vehicles 101, a management server, a global positioning server (GPS), a personal computer, a teleoperations system, a smartphone, or any computing device via the communication module 340. In general, control system 336 may cooperate at least with processor 304, propulsion system 308, navigation system 312, sensor system 324, and power system 332 to allow vehicle 101 to operate autonomously. That is, autonomous vehicle 101 is able to operate autonomously through the use of an autonomy system that effectively includes, at least in part, functionality provided by propulsion system 308, navigation system 312, sensor system 324, power system 332, and control system 336.

As will be appreciated by those skilled in the art, when autonomous vehicle 101 operates autonomously, vehicle 101 may generally operate, e.g., drive, under the control of an autonomy system. That is, when autonomous vehicle 101 is in an autonomous mode, autonomous vehicle 101 is able to generally operate without a driver or a remote operator controlling autonomous vehicle. In one embodiment, autonomous vehicle 101 may operate in a semi-autonomous mode or a fully autonomous mode. When autonomous vehicle 101 operates in a semi-autonomous mode, autonomous vehicle 101 may operate autonomously at times and may operate under the control of a driver or a remote operator at other times. When autonomous vehicle 101 operates in a fully autonomous mode, autonomous vehicle 101 typically operates substantially only under the control of an autonomy system.

Figure 4:
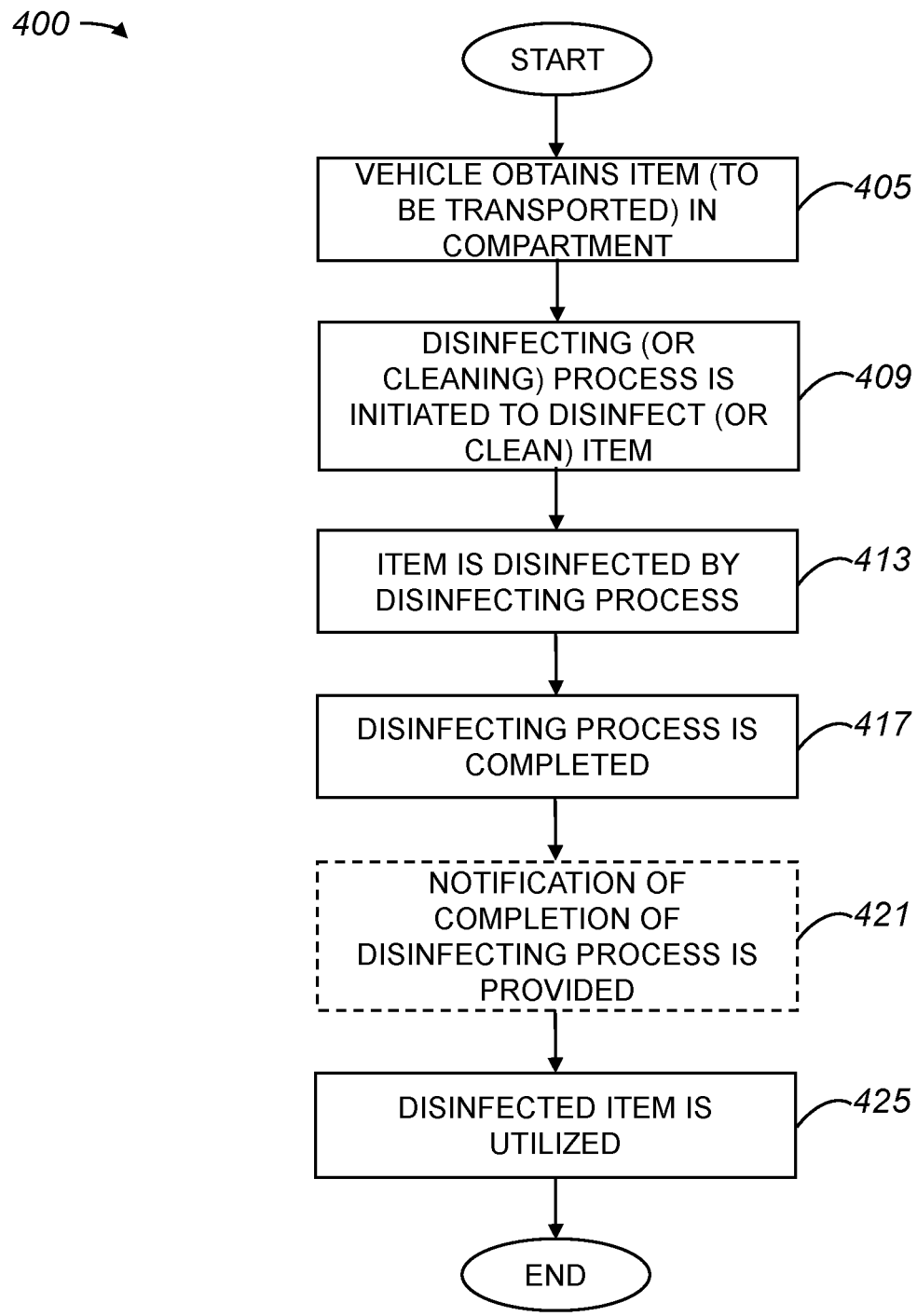
FIG. 4 is a process flow diagram which illustrates a method of disinfecting devices or items associated with medical services in accordance with an embodiment.

The ability to disinfect or to otherwise clean items such as devices which support medical services allows for contaminants to be removed from the devices and, thus, substantially reduce the likelihood that an individual receiving medical services may be adversely affected by the contaminants, e.g., that an individual may be less likely to become ill from the contaminants. FIG. 4 is a process flow diagram which illustrates a method of sanitizing or disinfecting devices or items associated with medical services in accordance with an embodiment. A method 400 of sanitizing or disinfecting a device or an item carried in a compartment of a vehicle begins at a step 405 in which the vehicle, e.g., an autonomous vehicle, obtains an item that is to be transported or otherwise carried on the vehicle. The item, which may be a medical device or an item that supports a medical service, may be received in a compartment of the vehicle.

Once the item is received in the compartment, a disinfecting or cleaning process is initiated in a step 409 to disinfect or to otherwise clean the item. A disinfecting or cleaning process may be initiated, in some instances, any time an item is received in a compartment and/or any time the item is determined to be contaminated or in need of a disinfecting or cleaning process. Such a process may be initiated substantially automatically, e.g., upon the item being placed in the compartment and the closing of a door on the compartment or upon the item being determined to need disinfecting or cleaning, or may be initiated at the request of an individual who is to obtain a service or to provide a service associated with the item. An individual may send a request either to a fleet management system or substantially directly to the vehicle to request that the item be disinfected or cleaned. Further, a disinfecting or cleaning process may be initiated at substantially any time between when a vehicle obtains an item and when the item is ready to be used. In one embodiment, a disinfecting or cleaning process occurs while the vehicle is driving from a source destination to a location at which an individual is to effectively utilize the item.

The item is disinfected by a disinfecting process in a step 413. In general, a disinfecting process may be any suitable process which allows the item and, by extension, at least part of the compartment that the item is in, to be disinfected, sanitized, decontaminated, sterilized, purified, and/or otherwise cleaned. Processes may include, but are not limited to including, a process which involves the application of waves of any wavelength suitable for providing disinfecting capabilities such as light in the UV spectrum, a process which involves the application of heat, and/or a process which involves the application of chemicals such as disinfecting or cleaning agents.

In a step 417, the disinfecting process is completed. That is, in step 417, the item is disinfected or cleaned to a desired level. Factors which determine a desired level may vary widely. By way of example, the item may be considered to be disinfected based on an amount of time associated with the disinfecting process, a strength of a UV light, an amount of heat applied to the item, and/or a contaminant or pathogen level associated with the item. In one embodiment, a sensor may be located in a compartment of a vehicle, and arranged to detect a pathogen level. Such a sensor may detect a pathogen level at the time the item is placed in the compartment, and the pathogen level may be used to determine an amount of disinfecting or cleaning necessary to reach the desired level, or even whether a disinfecting or cleaning process is necessary.

In an optional step 421, a notification of a completion of a disinfecting process may be provided. Such a notification may be provided substantially directly to an individual who is expecting to receive a service associated with the item or an individual who is expected to effectively administer a service using the item, e.g., a medical professional. The notification may instead be provided to a fleet management system, and the fleet management system may notify the individual that the item has been disinfected or cleaned. In one embodiment, measurement of contaminant or pathogen levels associated with the item that has been disinfected may be taken before and after the disinfecting process, and the notification may include a report which identifies the measurements.

From step 417 or from optional step 421, process flow moves to a step 425 in which the disinfected item is utilized. In other words, the disinfected item is used by an individual. After the disinfected item is utilized by the individual, the method of sanitizing or disinfecting a device or an item carried in a compartment of a vehicle is completed.

As mentioned above, while a disinfecting process may be substantially automatic, i.e., assumed to be requested as a default, an individual may be tasked with requesting a disinfecting process. For example, an individual may access a customer portal such as an online customer portal, or send a text to a particular number to activate a disinfecting process. In one embodiment, at least one camera may be installed in a compartment of a vehicle to allow a customer to watch a video or still feed from the camera while the disinfecting process is ongoing. Further, a vehicle may provide the customer with sensor data or information associated with the disinfecting process, e.g., the vehicle may provide a pathogen level to the customer.

Figure 5:
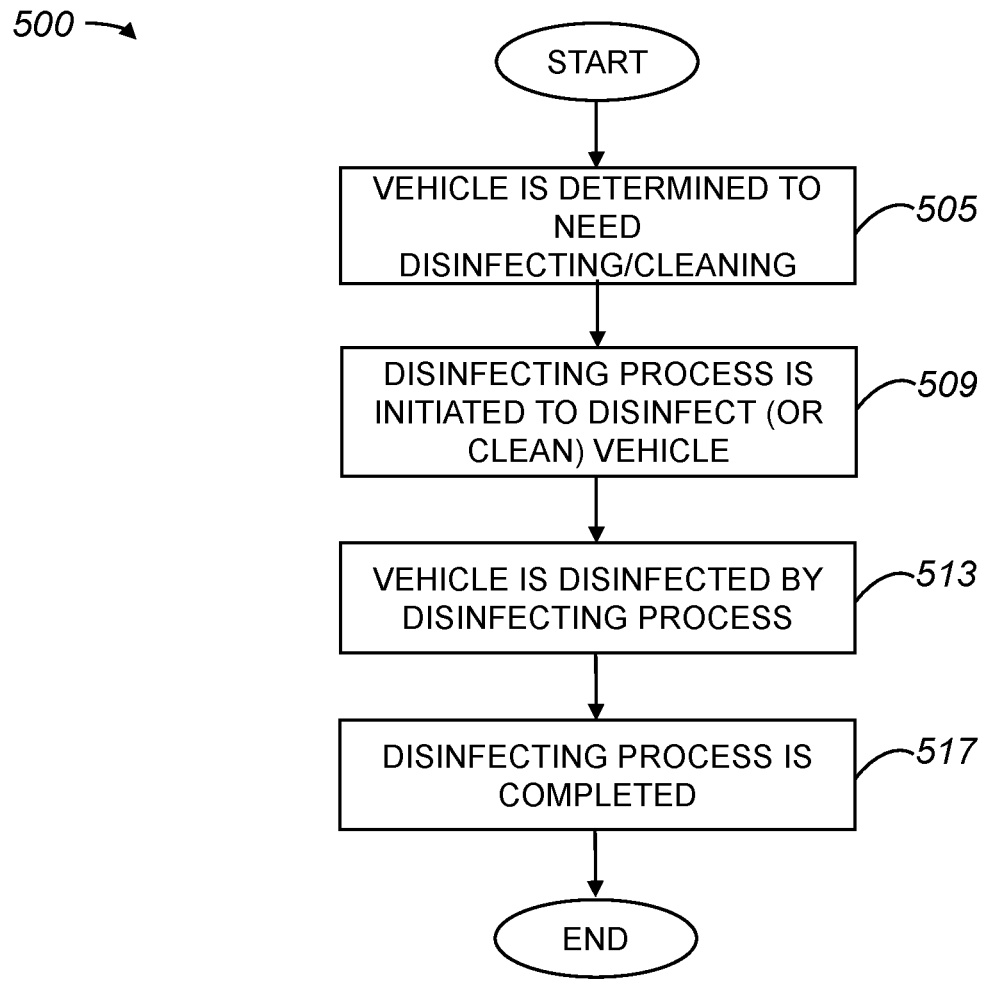
FIG. 5 is a process flow diagram which illustrates a method of disinfecting a vehicle in accordance with an embodiment.

It may be desirable to disinfect or sanitize a vehicle periodically to decrease the likelihood that the vehicle may carry a contaminant or a pathogen. Referring next to FIG. 5, a method of disinfecting a vehicle will be described in accordance with an embodiment. A method 500 of disinfecting a vehicle begins at a step 505 in which it is determined that a vehicle needs disinfecting or cleaning. A vehicle may be identified as in need of disinfecting or cleaning using any suitable metric. Suitable metrics include, but are not limited to including, a contamination level present on an exterior of the vehicle as measured using sensors, an amount of time that has elapsed since a most recent disinfecting process, a number of services provide since a most recent disinfecting process, a number of individuals serviced by the vehicle since a most recent disinfecting process, etc. Although the entire vehicle may be disinfected or cleaned in step 505, in some embodiments, different parts of the vehicle may be identified for cleaning and subsequently cleaned. For example, relatively high touch areas such as the doors of a compartment may be cleaned, a customer interface screen such as a human machine interface (HMI) on the vehicle may be cleaned, and/or a windshield on the vehicle may be cleaned.

After it is determined that the vehicle would benefit from a disinfecting or cleaning process, a disinfecting process is initiated in a step 509. The disinfecting process may include the use of cleaning solutions and mechanical dispensing devices. The disinfecting process may be initiated substantially automatically upon a determination of a need for disinfecting, or the disinfecting process may be initiated substantially manually, e.g., through a fleet management system. In a step 513, the vehicle is disinfected by the disinfecting process. The disinfecting process is completed in a step 517. Upon the completion of the disinfecting process, the method of disinfecting a vehicle is completed.

A vehicle such as an autonomous vehicle which is configured to provide medical services may have compartments which may be accessed in a contactless manner. When an individual may gain access to the contents of a compartment of an autonomous vehicle in a substantially contactless manner, the individual may avoid touching the vehicle. As a result, the individual is less likely to be affected by any contaminants which may be present on or in the vehicle.

Figure 6A:
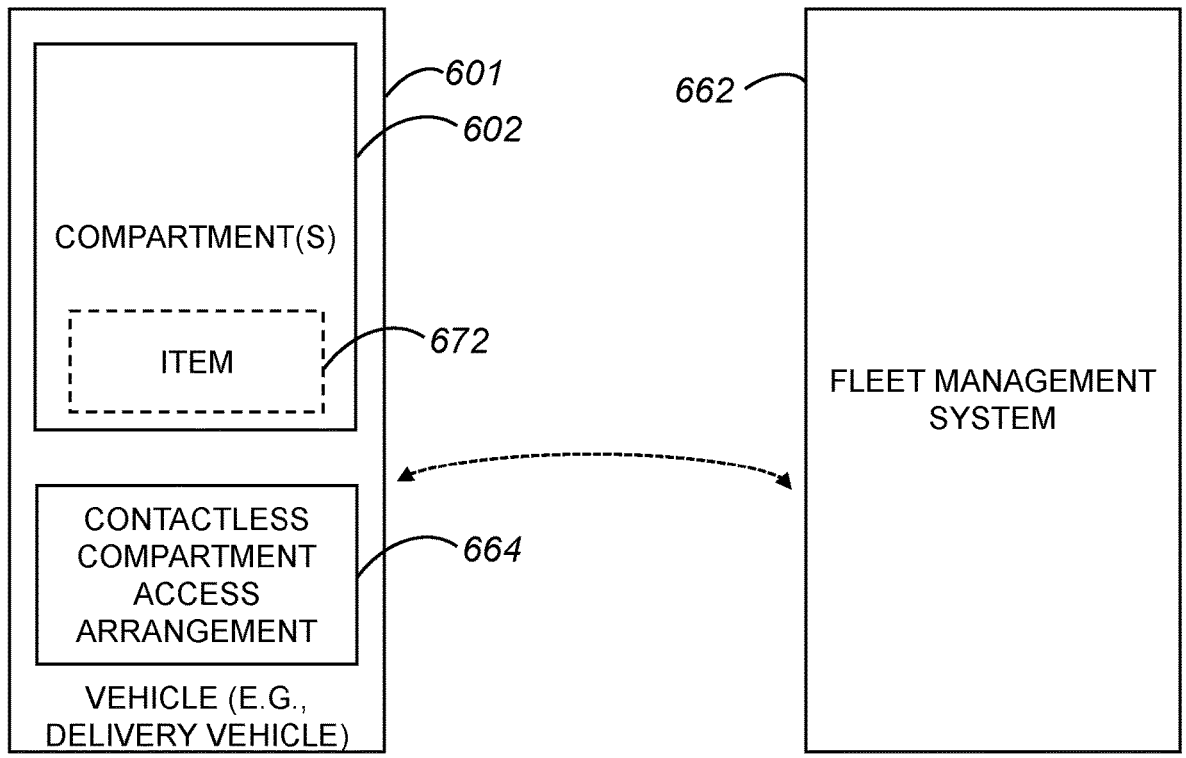
FIG. 6A is a diagrammatic representation of a delivery vehicle with a contactless compartment access arrangement that is utilized by a fleet management system to allow access to a compartment in accordance with an embodiment.
Figure 6B:
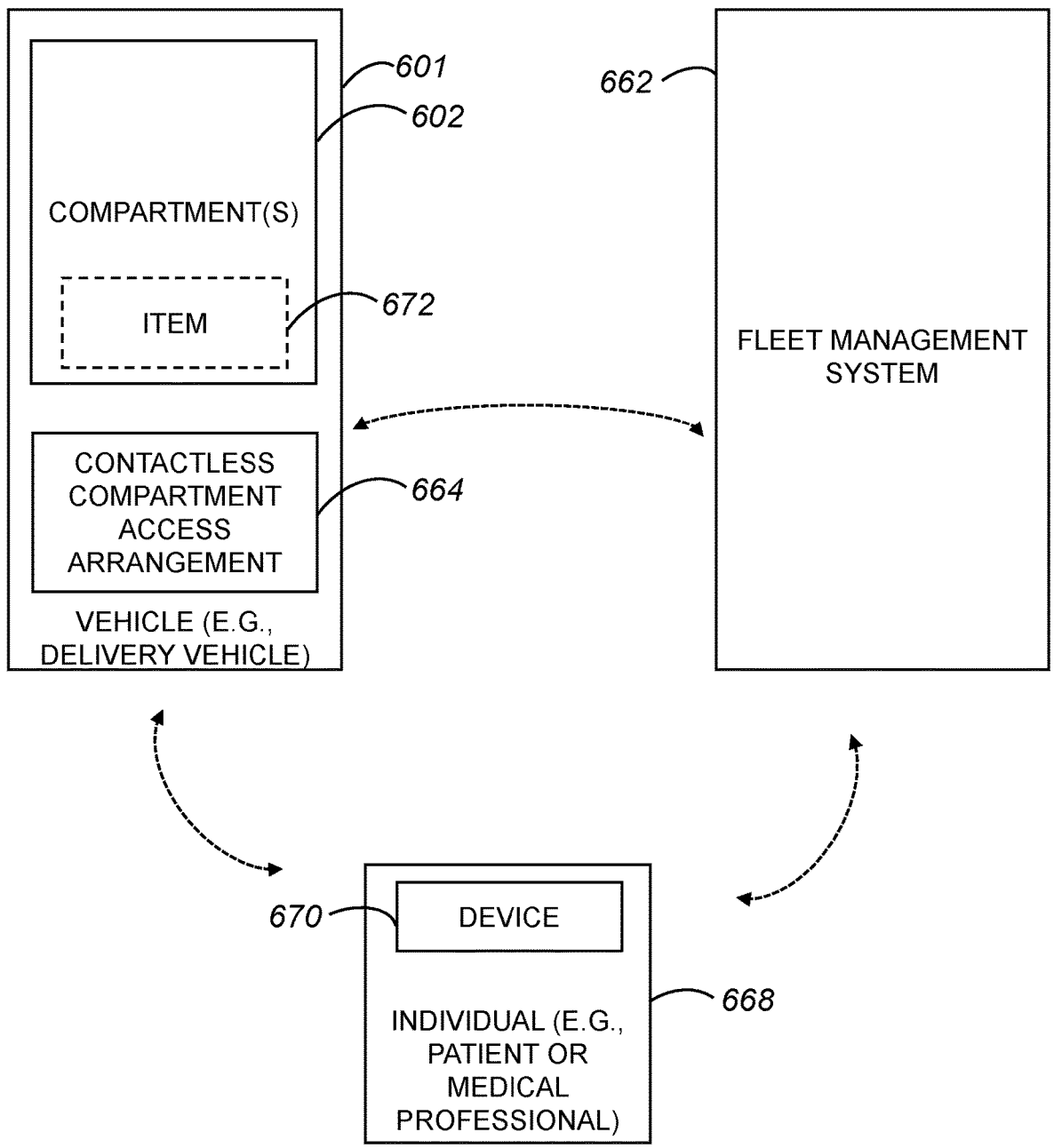
FIG. 6B is a diagrammatic representation of a delivery vehicle, e.g., delivery vehicle 601 of FIG. 6A, in which a contactless compartment access arrangement is arranged to be utilized by a customer and/or a fleet management system, e.g., fleet management system 662 of FIG. 6A, in accordance with an embodiment.

Referring next to FIG. 6A, a delivery vehicle with a contactless compartment access arrangement that is utilized by a fleet management system to allow an individual to access to a compartment of the vehicle will be described in accordance with an embodiment. A vehicle 601, which may be an autonomous vehicle, includes at least one compartment 602 in which an item 672 is contained.

Compartment 602 is arranged to be accessed in a contactless manner. That is, an individual may access compartment 602 to retrieve item 672 without having to make physical contact with vehicle 601. A contactless compartment access arrangement 664 may be a part of vehicle 601, and may be arranged to communicate with a fleet management system 662 to cause compartment 602 to be opened, e.g., to unlock and open a door on compartment 602. Fleet management system 662 may generally be arranged to coordinate services and to support services provided by a fleet of vehicles such as vehicle 601. Fleet management system 662 may, in one embodiment, determine that vehicle 601 is ready to provide a service using item 672, and may communicate with contactless compartment access arrangement 664 to effectively provide instructions to open compartment 602. Upon receiving instructions from fleet management system 662, contactless compartment access arrangement 664 may cause compartment 602 to be opened, e.g., to cause a door on compartment 602 to be unlocked and opened. As will be appreciated by those skilled in the art, any suitable types of communications may be used to enable vehicle 601 to communicate with fleet management system 662. For example, wireless communications such as cellular communications, Wi-Fi communications, and/or 3G/4G/5G communications may be used.

In one embodiment, an individual may substantially directly cause compartment 602 to open without physically touching vehicle 601. FIG. 8B is a diagrammatic representation of delivery vehicle 601 in which contactless compartment access arrangement 664 is arranged to be utilized by an individual and/or fleet management system 662 in accordance with an embodiment. An individual 668, who may be a patient or a medical professional, may have a device 670 such as a smartphone, a cell phone, a tablet computer, a laptop computer, or a desktop computer. Device 670 may be used to substantially directly instruct contactless compartment access arrangement 664 to provide access to compartment 602. Device 670 may engage in cellular communications, Wi-Fi communications, Bluetooth communications, and/or 3G/4G/5G with vehicle 801. For example, device 670 may send a text which causes compartment 602 to become accessible, or device 670 may be used to access an application or a web interface which allows individual 668 to effectively control the opening of compartment 602. It should be appreciated that in some embodiments, individual 668 may be expected to undergo an authorization or authentication process to verify his or her identity before being allowed access to item 672. For example, individual 668 may provide information such as a password to a fleet management system using device 670 in order to be granted access to item 672.

Alternatively, device 670 may communicate with fleet management system 662, as for example using communications such as cellular communications, Wi-Fi communications, and/or 3G/4G/5G communications. When device 670 communications with fleet management system 662, fleet management system 662 may communicate substantially directly with vehicle 601 to provide access to compartment 602.

In one embodiment, contactless compartment access arrangement 664 may be arranged to provide access to compartment 602 based upon physical actions of customer 668. Contactless compartment access arrangement 664 may include at least one sensor arranged to enable individual 662 to gain access to compartment 602. Suitable sensors include, but are not limited to including, motion sensors, cameras, RFID readers, and/or microphones. A motion sensor may sense when individual 668 is making a motion intended to cause compartment 602 to become accessible, e.g., individual 662 may wave at the motion sensor or may kick a foot under a motion sensor. A camera may be used to verify the identity of individual 662, and to open a door to compartment 602 when individual 662 is determined to be in close proximity to vehicle 601. An RFID reader may be used to scan an ID card or badge in the possession of individual 662, and to enable access to compartment 602 upon authenticating the ID card or badge. NFC technology may also be used to open a door to compartment 602 when individual 662 presents his or her smartphone. A microphone may be used to pick up voice commands from individual 662 such as a spoken password. A text or SMS message may be sent by individual 662, or an online portal may be used by individual 662, to cause the door to compartment 602 to open.

An autonomous delivery vehicle may generally be used to provide medical support when medical care is not readily accessible. For example, in some rural areas, patients may be required to drive significant distances to receive medical care. Alternatively, in situations in which shelter-in-place and/or stay-at-home orders are in effect, individuals may not wish to or be able to visit medical care facilities. Thus, configuring an autonomous delivery vehicle to facilitate providing medical support may make medical care more accessible. An autonomous delivery vehicle configured to provide medical support may also be used at a public location, e.g., in a park or in a parking lot, such that groups of potential patients may be efficiently serviced by the vehicle.

To configure an autonomous vehicle to provide medical support, diagnostic equipment may be provided onboard the autonomous vehicle, as for example in a compartment onboard the autonomous vehicle. In addition, mechanisms which are arranged to administer tests, vaccinations, and the like may also be provided onboard the autonomous vehicle, along with communications equipment which may facilitate the interaction of a patient with a medical profession at a remote location with respect to the autonomous vehicle. By way of example, an autonomous vehicle configured to provide medical support may be utilized in a temporary location such as a parking lot that is designated as a medical testing site.

Figure 7:
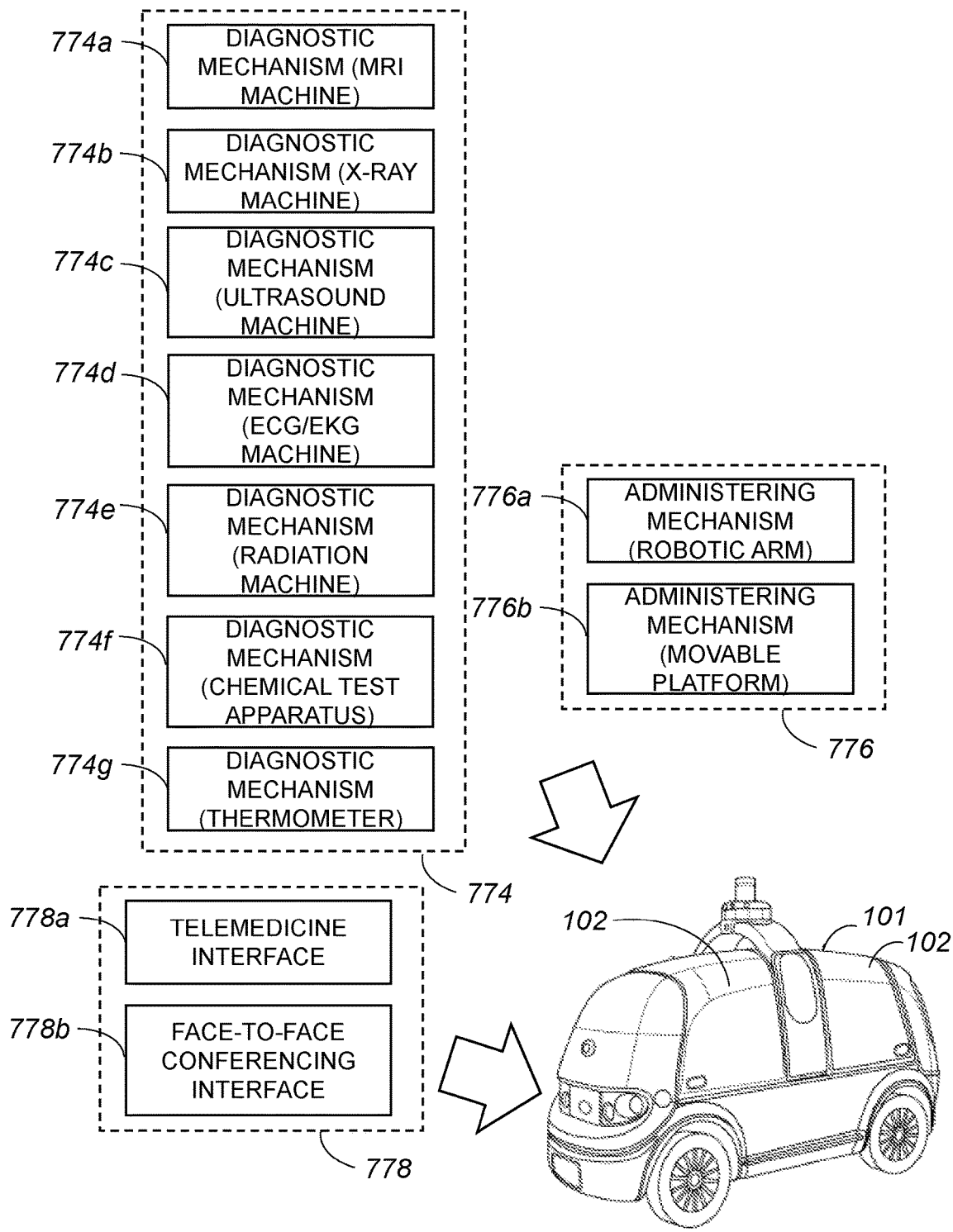
FIG. 7 is a diagrammatic representation of an autonomous vehicle, e.g., autonomous vehicle 101 of FIGS. 1-3, in which compartments are arranged to carry components which support medical procedures in accordance with an embodiment.

FIG. 7 is a diagrammatic representation of an autonomous vehicle, e.g., autonomous vehicle 101 of FIGS. 1-3, in which compartments are arranged to carry components which provide medical support in accordance with an embodiment. Autonomous vehicle 101, a shown, includes two compartments 102. It should be appreciated, however, that autonomous vehicle 101 may generally include any number of compartments 102, and may include a single compartment or may include more than two compartments 102.

Compartments 102 may be arranged to carry diagnostic equipment 774, administering mechanisms 776, and teleconferencing equipment 778. Diagnostic equipment 774 generally includes, but is not limited to including, medical equipment that may allow diagnostic information to be obtained from a patient to facilitate the diagnosis of an illness, injury, or other affliction. Administering mechanisms 776 are mechanisms which enable medical treatment such as vaccines to be administered to a patient, e.g., when a medical professional at a remote location controls the mechanisms, and also facilitate the use of diagnostic mechanisms 774. Teleconferencing equipment 778 generally includes components which effectively allow vehicle 101 to serve as an endpoint in a teleconference. As will be appreciated by those skilled in the art, teleconferencing equipment 778 may include a display screen, a network interface that allows for wireless communications, an audio output device such as a speaker, and an audio input device such as a microphone. Teleconferencing equipment 778 may also include a computing device. In one embodiment, teleconferencing equipment 778 may be a smartphone that is used to provide vehicle 101 with endpoint capabilities, e.g., the smartphone may be used to effectively enable vehicle 101 to serve as an endpoint in a teleconference by providing a display screen, a network interface, a speaker, and a microphone.

Diagnostic equipment 774 may be substantially permanently fixed in one of compartments 102. Alternatively, diagnostic equipment 774 may be configured as modular inserts which may be efficiently swapped into and out of compartments 102 as needed. It should be appreciated that upon installation of diagnostic equipment in one of compartments 102, diagnostic equipment 774 may be calibrated to ensure proper performance.

Diagnostic equipment 774 may generally include any suitable diagnostic apparatus such as apparatus that may be found in a medical facility. Diagnostic equipment may include, but is not limited to including, a magnetic resonance imaging (MRI) machine 774a, an X-ray machine 774b, an ultrasound machine 774c, an echocardiogram/electrocardiography (ECG/EKG) machine 774d, a radiation machine 774e, a chemical test apparatus 774f, and a thermometer 774g. MRI machine 774a is arranged to obtain MRI images of a patient. X-ray machine 774b is arranged to obtain x-ray images of a patient. Ultrasound machine 774c is arranged to obtain ultrasound images of a patient, and may include a wand that is arranged to be scanned over the patient. ECG/EKG machine 774d is arranged to measure electrical activity of the heart of a patient by monitoring electrical impulses associated with heartbeats, and may include electrodes which are to be attached to a patient. Radiation machine 774c, which includes devices other than x-ray machines which utilize radiation for medical purposes, may obtain images of a patient through fluoroscopy or computed tomography (CT) scans. Chemical test apparatus 774f may include a component that is arranged to obtain a biological specimen, e.g., blood or saliva, from a patient and to perform a chemical test on the biological specimen. Thermometer 774g may be arranged to take the temperature of a patient either through physical contact with the patient or without physically contact with the patient, e.g., thermometer 774b may be an infrared thermometer.

Any information obtained using diagnostic equipment 774 may be uploaded to a server, e.g., a cloud server, using a communications interface such as communications system 340 of FIG. 3. In general, the information obtained using diagnostic equipment 774 may relate to a physical condition of a patient and may include, but is not limited to including, biological information associated with the patient, health information associated with the patient, and/or physical information associated with a patient. Information on a server may be accessed by a medical professional. Alternatively, information obtained using diagnostic equipment 774 may be stored in memory onboard the vehicle.

Administering mechanisms 776 include, but are not limited to including, a robotic arm 776a and a movable platform 776b. Robotic arm 776a may be arranged to be controlled by a medical professional at a remote location, or robotic arm 776a may include sensors which allow robotic arm 776a to sense how to move in order to perform a procedure on a patient. Robotic arm 776a may include a claw or other grasping mechanism that allows robotic arm 776a to hold an object such as a syringe, a test tube, or a thermometer such as thermometer 774g. Movable platform 776b may be arranged to have a diagnostic equipment 774 mounted thereon, such that platform 776b may effectively move diagnostic equipment 774 into a position that facilitates performing a medical procedure on a patient. For example, thermometer 774g may be mounted on movable platform 776b such that movable platform 776b may effectively raise or lower thermometer 774g to the level of a forehead of a patient.

Teleconferencing equipment 778 includes at least a telemedicine interface 778a and a face-to-face conferencing interface 778b. In general, teleconferencing equipment 778 utilizes telecommunications technology to support communications between different endpoints or locations.

Telemedicine interface 778b may allow a remote medical professional to see and to manipulate diagnostic equipment 774 and/or administering mechanisms 776. Face-to-face conferencing interface 778b may include a display screen, a communications interface, and other components which allow a patient to participate in a telemedicine session with a remote medical professional or a remote party. In general, teleconferencing equipment 778 may utilize communications system 340 of FIG. 3 to support communications with a medical professional and an ability for the medical professional to manipulate diagnostic equipment 774 and/or administering mechanisms 776. It should be appreciated, however, that teleconferencing equipment 778 may include its own capabilities to communicate wirelessly with an endpoint, e.g., an endpoint at which the medical professional is located.

A telemedicine session may generally be supported by teleconferencing equipment 778 such as telepresence equipment, and enables a service provider, e.g., a medical professional, to communicate with a service recipient, e.g., a patient, when the service provider and the service recipient are remote with respect to each other. As will be appreciated by those skilled in the art, telemedicine enables a medical professional to provide a remote diagnosis and a remote treatment of a patient through the use of teleconferencing equipment 778, and effectively facilitates the sharing of medical information between different location, e.g., a location at which a patient is located and a location at which a medical professional is located, using teleconferencing equipment 778.

Figure 8:
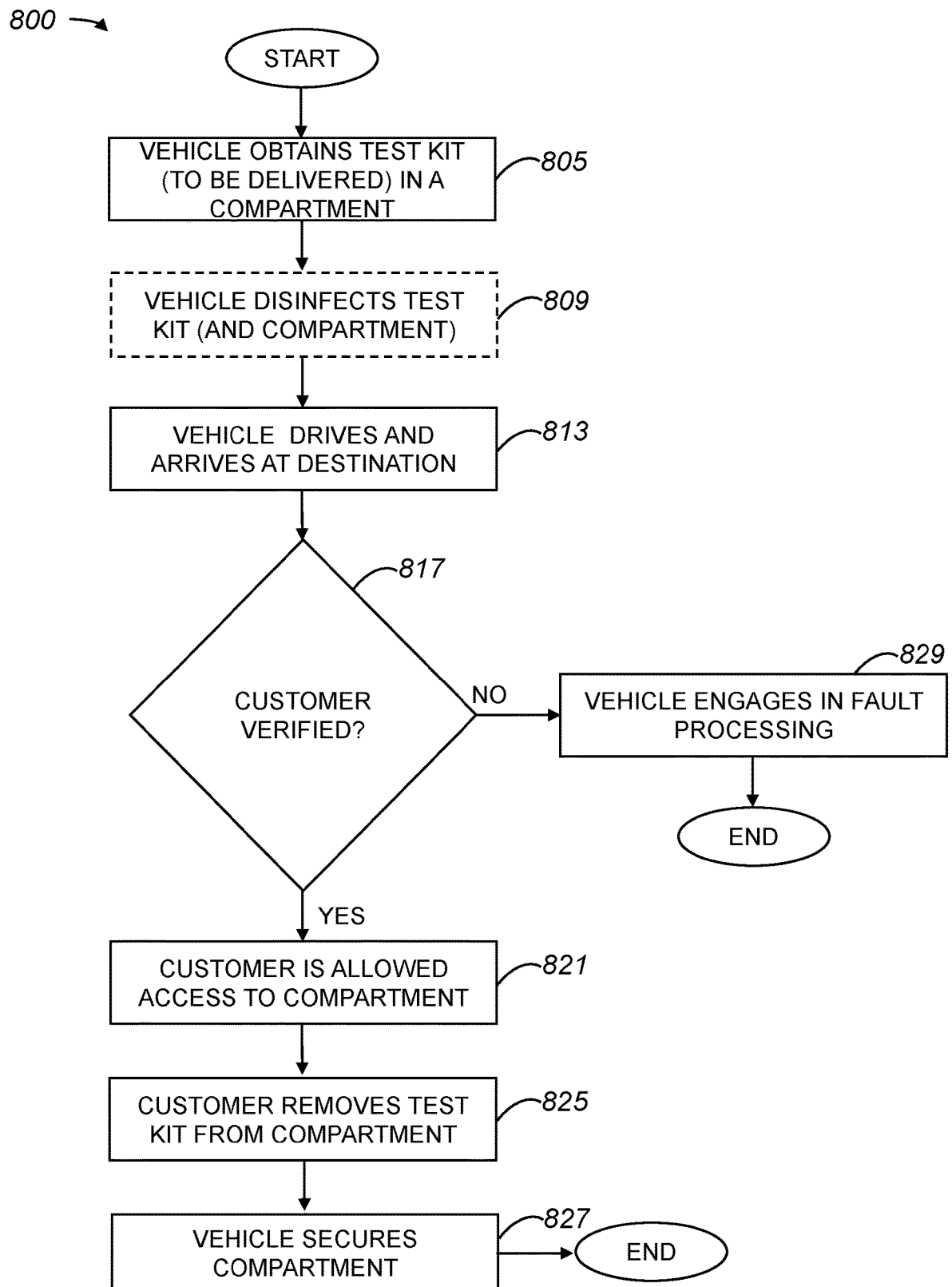
FIG. 8 is a process flow diagram which illustrates a method of providing a test kit to a customer using an autonomous delivery vehicle in accordance with an embodiment.

In one embodiment, an autonomous vehicle may be used to deliver equipment that may be used by a customer, or a service recipient, to administer a medical test on himself or herself. FIG. 8 is a process flow diagram which illustrates a method of providing a test kit to a customer using an autonomous delivery vehicle in accordance with an embodiment. A method 800 of providing a test kit to a customer begins at a step 805 in which a vehicle, e.g., autonomous vehicle 101 of FIG. 2, obtains a test kit that is to be delivered in a compartment of the vehicle to a destination. The test kit may be obtained from a government agency, e.g., the Center for Disease Control (CDC), or from a medical office or hospital. In some instances, a test kit may be obtained from a retailer or from a manufacturer of the test kit.

In an optional step 809, the vehicle may disinfect the test kit, as well as the compartment. The vehicle arrives at a destination in a step 813. Typically, the destination is where a customer will receive the test kit. At the destination, a determination is made in a step 817 as to whether the customer receiving the test kit is verified. As will be appreciated by those skilled in the art, medical tests are often labeled with patient names to make sure the collected specimens are associated with the correct patient. Thus, determining whether the customer is verified may include determining whether the customer has identification that matches the patient name associated with the test kit. In general, verifying the customer may include the customer providing a password or other identifying information. Verifying the customer may include, in one embodiment, the vehicle and/or a fleet management system engaging in communications with the customer, e.g., a representative at a fleet management system may communicate with the customer via a device such as a smartphone or via a communications device of the vehicle.

If the determination is that the customer is not verified, then process flow moves from step 817 to a step 829 in which the vehicle engages in fault processing. Fault processing may include, but is not limited to including, contacting the organization that provided the test kit, contacting the customer, determining whether there is another way to verify the identity of the customer, and/or leaving the destination without delivering the test kit. Once the vehicle engages in fault processing, the method of providing a test kit to a customer is terminated.

Returning to step 817, if the determination is that the customer has been verified, the implication is that the customer is the intended receipt of the test kit or is authorized to obtain the test kit. Accordingly, in a step 821, the customer is allowed to access the compartment in which the test kit is located. Allowing the customer access to the compartment may include, but is not limited to including, providing access in a contactless manner, or providing access when the customer interfaces with a keypad or other input device on the vehicle.

Once the customer is allowed access to the compartment, the customer removes the test kit from the compartment in a step 825. Upon the customer removing the test kit, the vehicle secures the compartment in a step 827, and the method of providing a test kit to the customer is completed. It should be appreciated that in some instances, the vehicle may leave the destination once the vehicle secures the compartment.

Figure 9:
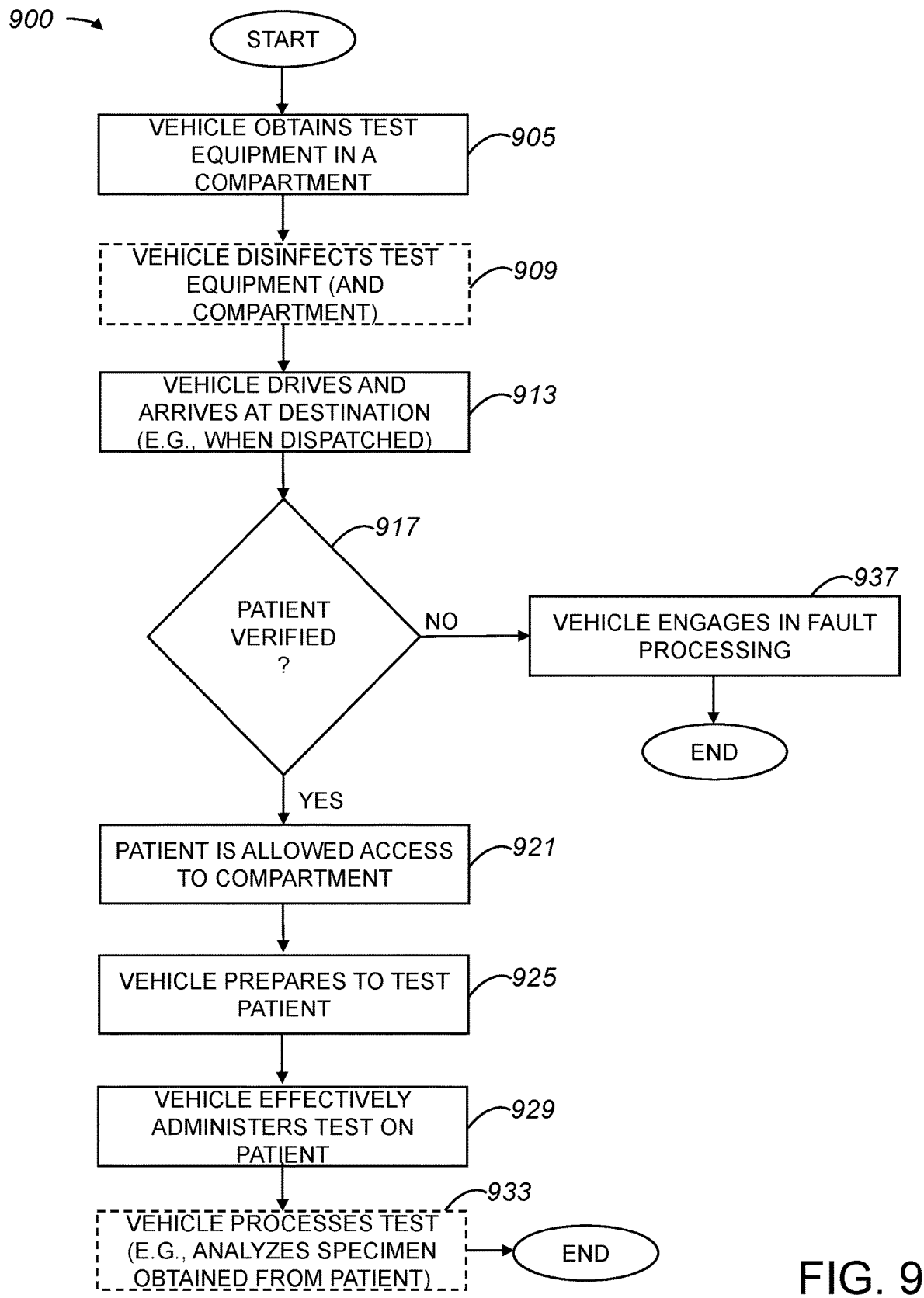
FIG. 9 is a process flow diagram which illustrates a method administering a testing on a patient using an autonomous vehicle in accordance with an embodiment.

In one embodiment, a vehicle may be configured to administer or perform a test on a patient. For example, the vehicle may include a robotic arm that may be manipulated either by a remote operator and/or through the use of sensors to swab a nasal cavity of a patient. FIG. 9 is a process flow diagram which illustrates a method of administering or performing a test on a patient using equipment on an autonomous vehicle in accordance with an embodiment. A method 900 of administering or performing a test on a patient begins at a step 905 in which test equipment is loaded into a compartment on a vehicle, e.g., autonomous vehicle 101 of FIG. 2. The test equipment may be loaded into the compartment on the vehicle, for example, by a fleet manager or by individuals affiliated with a medical organization. In one embodiment, a first compartment on the vehicle may be arranged to contain components which support performing a test, and a second compartment on the vehicle may be arranged to contain components which process specimens and/or information obtained from the test. Obtaining test equipment may include, but is not limited to including, installing a modular insert which contains the test equipment into a compartment.

In an optional step 909, the vehicle may disinfect the test equipment as well as the compartment. It should be appreciated that the test equipment may be disinfected while the vehicle is in transit to a destination.

The vehicle arrives at a destination in a step 913. The vehicle may travel to and arrive at the destination when dispatched by a fleet management system or a medical organization. In one embodiment, the vehicle travels autonomously to the destination, e.g., the destination at which the patient is located. Once the vehicle arrives at the destination, the patient may effectively interact with the vehicle, and it is determined in a step 917 whether the patient is verified. A determination of whether a patient is verified may effectively be a determination of whether the patient is who he or she purports to be. Such a determination may include, but is not limited to including, authentication processes such as checking an ID card of the patient, checking biometric data such as fingerprints of the patient, utilizing cameras and/or other sensors on the vehicle to identify the patient, etc.

If the determination in step 917 is that the patient is not verified, the indication is that either the patient is not who he or she purports to be, or that the patient has not provided sufficient proof of his or her identity. As such, the vehicle engages in fault processing in a step 937. Fault processing allows a determination to be made, e.g., in conjunction with a person associated with a fleet management system and/or a teleoperations system, as to what should be done to address the inability to verify the patient. Once fault processing is performed, the method of administering or performing a test on a patient is terminated.

Alternatively, if the determination in step 917 is that the patient is verified, the implication is that the patient may be tested. As such, in a step 921, the patient is allowed access to the compartment in which the test equipment is stored. Allowing the patient access generally involves opening a door or otherwise opening the compartment, e.g., in a contactless manner by the vehicle.

After access to the compartment is provided, the vehicle prepares to test the patient in a step 925. Actions taken in preparation to test the patient may vary widely depending upon the test that is to be administered. For example, if the patient is to be subjected to a swab test, the vehicle test equipment may include a robotic arm which will grasp a swab in preparation for testing. If the patient is to be subjected to an x-ray, the vehicle test equipment may include an x-ray machine that will turn on and potentially move in preparation for taking an x-ray of the patient.

In a step 929, the vehicle administers the test on the patient. It should be appreciated that the vehicle administers the test using test equipment onboard the vehicle. In one embodiment, when the test is a swab test, a robotic arm may manipulate a swab into a nasal cavity or into the mouth of the patient to obtain a specimen.

In an optional step 933, the vehicle processes the test. For example, the vehicle may analyze a specimen obtained from the patient by adding chemicals to the specimen, as provided on a swab, to determine whether the specimen tests positive for a pathogen such as a virus. Chemicals may be added to the specimen using dispensers in a compartment of the vehicle, or a robotic arm on the vehicle may manipulate chemicals and the specimen. In one embodiment, one compartment on the vehicle may be dedicated to processing tests, e.g., such a compartment may contain a centrifuge or other equipment suitable for processing a specimen obtained from a patient. The vehicle may process the test with compartments secured, e.g., with compartment doors closed. In one embodiment, the vehicle may process the test as the vehicle is departing from the destination. Once the test is administered and, optionally, once the vehicle processes the test, the method of administering or performing a test on a patient is completed. It should be appreciated that if the vehicle does not process the specimen, the vehicle may deliver the specimen to a test processing facility.

Figure 10:
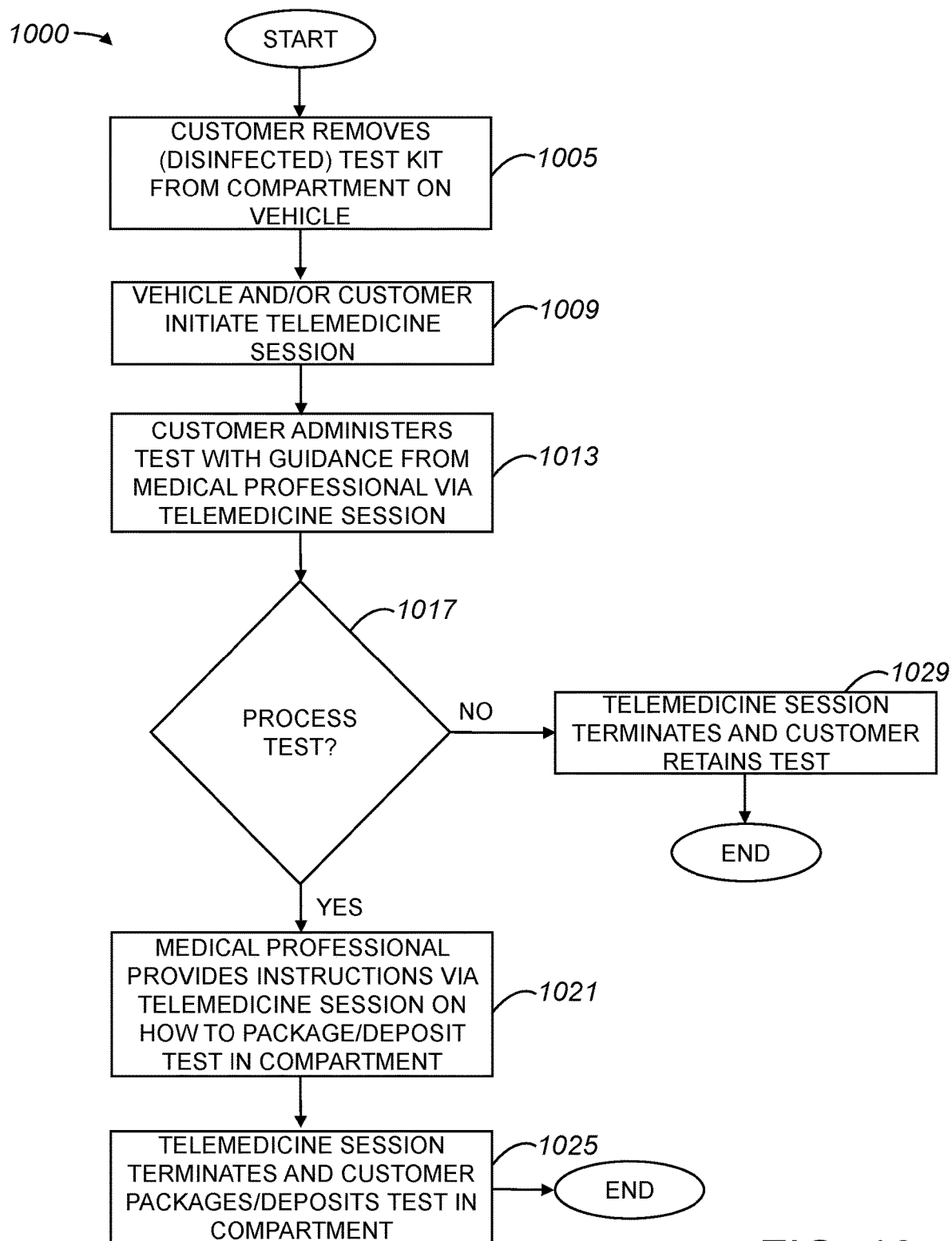
FIG. 10 is a process flow diagram which illustrates a method of providing medical guidance to a customer using an autonomous vehicle in accordance with an embodiment.

An autonomous vehicle may be used to support communications between a customer or a patient and a medical professional. For example, a customer may be asked to administer a test on himself or herself, while being guided through the process by a medical professional via a telemedicine session. FIG. 10 is a process flow diagram which illustrates a method of providing medical guidance to a customer using an autonomous vehicle in accordance with an embodiment. A method 1005 of providing medical guidance to a customer begins at a step 1005 in which a customer removes a test kit from a compartment on a vehicle such as autonomous vehicle 101 of FIG. 2. In one embodiment, the test kit is disinfected between a time at which the test kit is placed on the compartment and a time at which the customer removes the test kit from the compartment. It should be appreciated that customer may substantially be allowed to remove the test kit in the event that the customer is successfully authenticated.

In a step 1009, a telemedicine session is initiated. The telemedicine session, which generally involves a medical professional such as a doctor engaging in a virtual meeting or conference with a customer, may be initiated either by the vehicle or by the customer. In the described embodiment, the telemedicine session is supported using communications and video equipment onboard the vehicle. It should be appreciated, however, that in some embodiments, the telemedicine session may be supported using communications and video equipment in the possession of the customer. Initiating the telemedicine session may involve wireless communications between the vehicle and a device such as a cell phone or computing system in the possession of a medical professional or practitioner.

Once the telemedicine session is initiated, the customer may be guided by the medical professional to administer a test on himself or herself in a step 1013 using the test kit. For example, the medical professional may instruct the customer on how to swab himself or herself, how to draw blood from himself or herself, how to provide a saliva sample, etc.

In one embodiment, the vehicle may include equipment which allows specimens harvested or gathered by the customer to be processed onboard. By way of example, the vehicle may include equipment which adds chemical agents to a specimen in order to determine whether the specimen tests positive for a particular pathogen. In another embodiment, a specimen obtained from the customer may be placed in the vehicle and the vehicle may deliver the specimen to a testing facility such as a medical laboratory. As such, in a step 1017, it is determined whether the completed test, e.g., a specimen obtained using the test kit, is to be processed either onboard the vehicle or at a facility that the vehicle will deliver the test to.

If it is determined in step 1017 that the completed test is not to be processed either onboard the vehicle or at a facility such as a medical laboratory, then the telemedicine session terminates and the customer retains the test in a step 1029, and the method of providing medical guidance to a customer is completed. It should be appreciated that the customer may retain the test if results of the test may be readily obtained by the customer upon completing the test, e.g., if a positive result is visually self-evident. The customer may also retain the test if the customer is responsible for providing the test to a testing laboratory via a mail or package delivery service.

Alternatively, if it is determined in step 1017 that the completed test is to be processed either onboard the vehicle or at a facility such as a medical laboratory that is accessible to the vehicle, then the medical professional provides instructions via the telemedicine session in a step 1021. When the completed test includes a specimen to be processed by test equipment onboard the vehicle, the medical professional may instruct the customer on how to load the specimen into the test equipment or, more generally, how to deposit the specimen in a compartment. When the completed test includes a specimen to be transported to a facility by the vehicle, the medical professional may instruct the customer on how to package and to deposit the test in a compartment of the vehicle. It should be appreciated that materials for packaging the specimen may be provided onboard the vehicle.

After the medical professional provides instructions to the customer, the telemedicine session terminates, and the customer packages and/or deposits the completed test in a compartment of the vehicle in a step 1025. Once the completed test is placed in the compartment, the method of providing medical guidance to a customer is completed. The vehicle may secure compartments upon determining that the completed test has been placed in a compartment.

Figure 11:
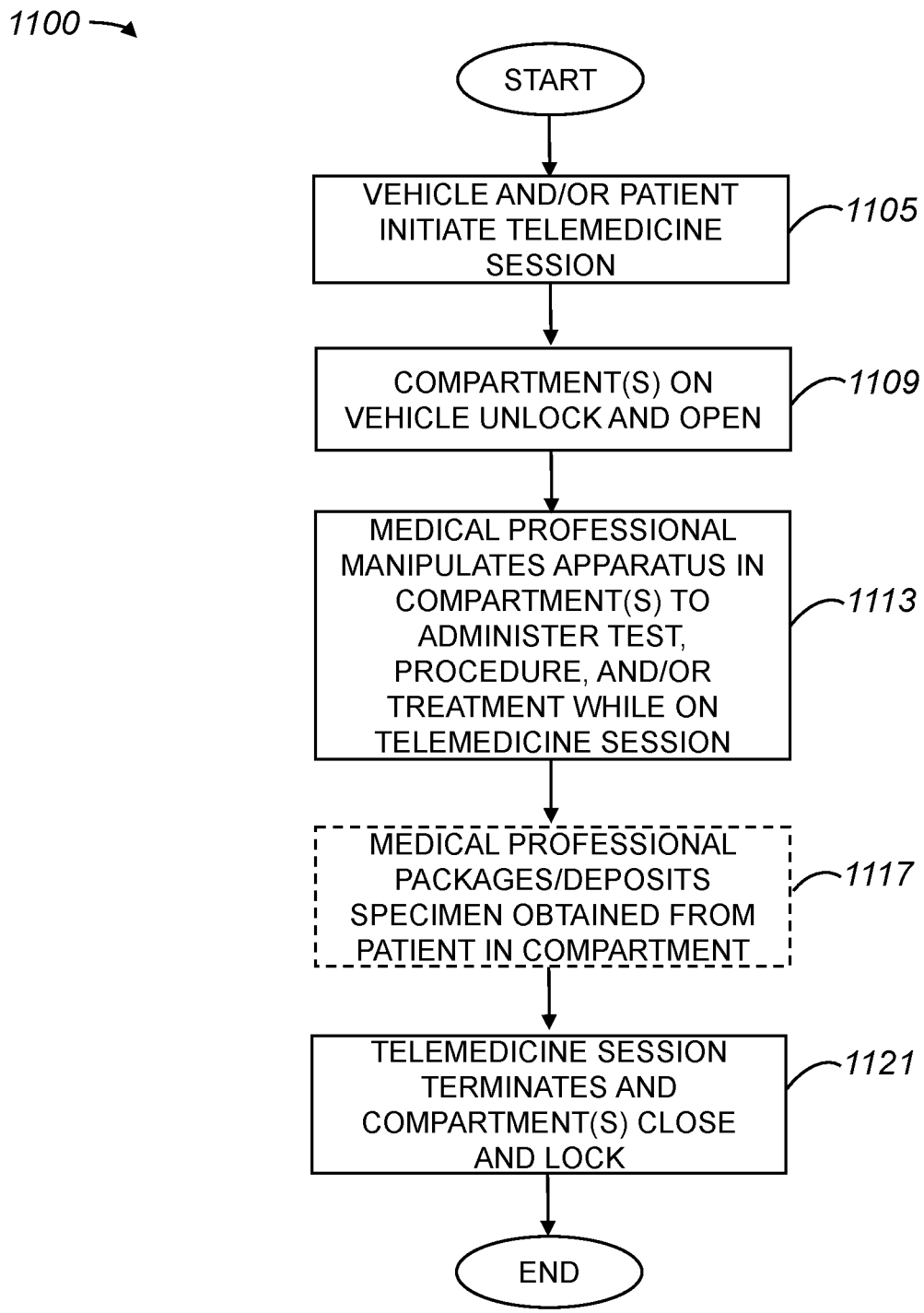
FIG. 11 is a process flow diagram which illustrates a method of executing or otherwise performing a medical procedure using an autonomous vehicle with a telemedicine interface in accordance with an embodiment.

In one embodiment, an autonomous vehicle may support the performance of a medical procedure such as a test, a treatment, and/or a vaccination during a telemedicine session. FIG. 11 is a process flow diagram which illustrates a method of executing, or administering, a medical procedure using an autonomous vehicle with a telemedicine interface in accordance with an embodiment. A method 1100 of executing a medical procedure in cooperation with a telemedicine session begins at a step 1105 in which a telemedicine session is initiated between a vehicle and a patient. The telemedicine session may involve a medical professional speaking with a patient through a display screen and microphone on the vehicle. The display screen and microphone may be part of a human machine interface (HMI) mounted on the vehicle that may be used to interact with the vehicle, of the display screen and microphone may be located in a compartment on the vehicle. The medical professional may be at a first endpoint that communicates with the patient using the vehicle, which is a second endpoint, via wireless communications. Alternatively, the medical professional may communicate with a patient through a display screen and microphone in the possession of the customer, e.g., through a display screen and microphone of a cell phone of the customer.

In a step 1109, at least one compartment of the vehicle is unlocked and opened. As discussed above, the compartment may be unlocked and opened in a contactless manner, or may be unlocked and opened when the patient physically touches the vehicle. The compartment generally contains an apparatus such as a diagnostic mechanism and/or and administering mechanism, as described above with respect to FIG. 7.

Once the compartment is unlocked and opened, the medical professional may manipulate the apparatus in a step 1113. The apparatus may be controlled by the medical professional to administer a test, administer a procedure such as a vaccination, and/or to provide treatment to the patient while the medical professional engages with the patient during the telemedicine session. The medical professional may operate the apparatus from a workstation that communicates with the apparatus to substantially control the apparatus using any suitable type of wireless communications. That is, the medical professional may manipulate the apparatus via teleoperations or a remote control. For example, if the apparatus is a robotic arm which holds a syringe containing a vaccine, the medical professional may remotely control the robotic arm to administer the vaccine to the patient.

In an optional step 1117, the medical professional may manipulate the apparatus to package and/or to deposit any specimen obtained from the patient into a compartment. It should be appreciated that if the medical procedure performed using the apparatus involved emptying a syringe, e.g., emptying a syringe to vaccinate the patient, then the syringe may be deposited in a compartment as medical or hazardous waste.

After the apparatus is manipulated by the medical professional, and/or after any specimen is optionally deposited in a compartment, the telemedicine session terminates and any compartments on the vehicle which have been opened are then closed and locked in a step 1121. In some situations, once the compartments are closed, the compartments may be substantially automatically disinfected. Once any previously open compartments are closed and locked, the method of executing or administering a medical procedure in cooperation with a telemedicine session is completed.

Figure 12:
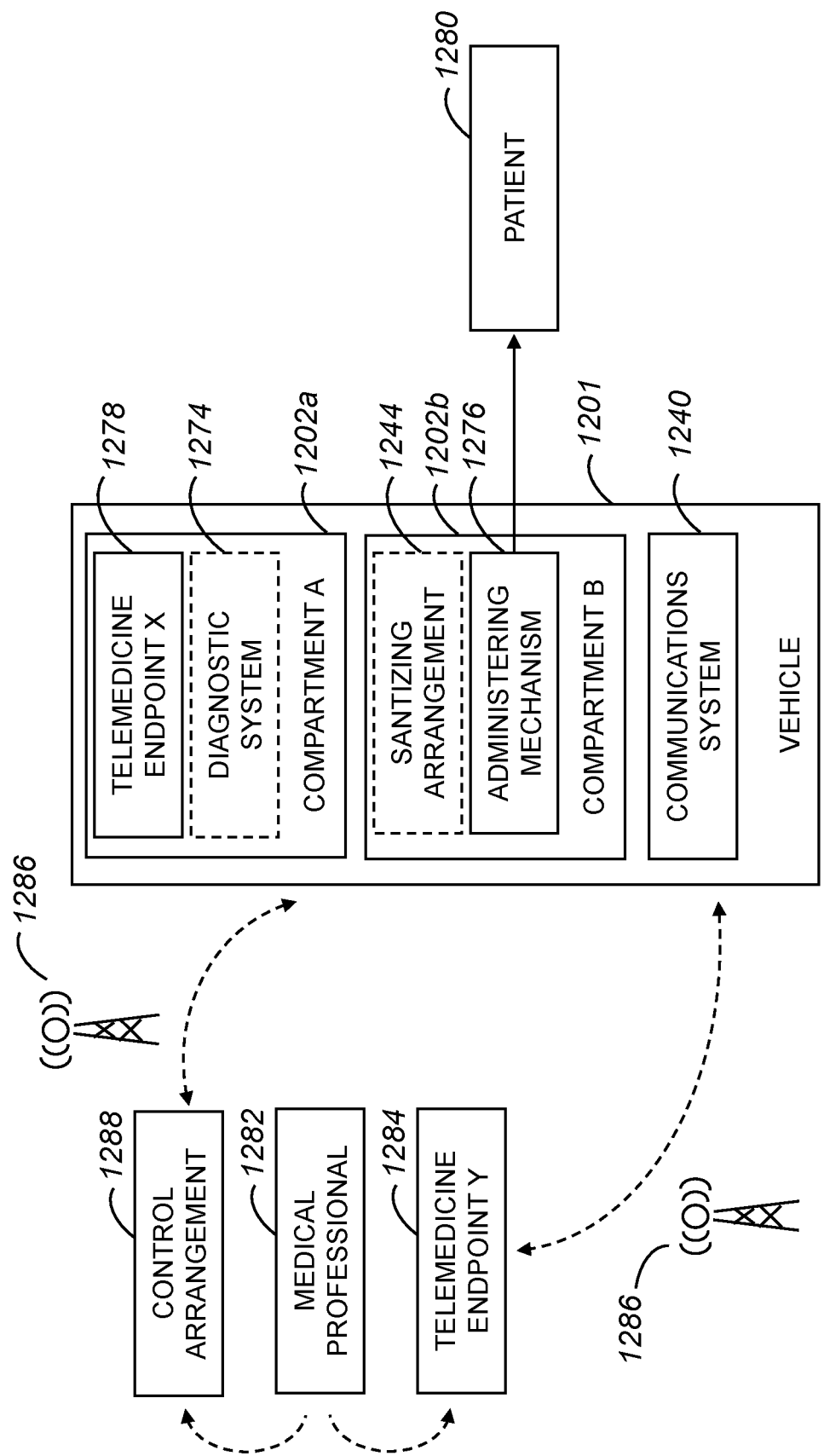
FIG. 12 is a block diagram representation of a system in which a medical professional may execute a medical procedure using an autonomous vehicle with a telemedicine interface in accordance with an embodiment.

FIG. 12 is a block diagram representation of a platform or a system in which a medical professional may execute a medical procedure using an autonomous vehicle with a telemedicine interface in accordance with an embodiment. A medical professional 1282 may be remote with respect to a vehicle 1201, which may be an autonomous vehicle that includes components of autonomous vehicle 101 of FIGS. 2 and 3. For ease of illustration, not all components shown vehicle 101 of FIGS. 2 and 3 have been shown in FIG. 12, although it should be appreciated that vehicle 1201 generally includes components of autonomous vehicle 101. Vehicle 1201 includes a first compartment 1202a and a second compartment 1020b, as well as a communications system 1240.

First compartment 1202a includes a telemedicine endpoint 1278 which includes apparatuses that may be used to support communications involving a patient 1280 using communications system 1240. That is, telemedicine endpoint 1278 may include, but is not limited to including, a display screen, a video camera, a microphone, a data entry arrangement such as a keyboard, and/or a computing arrangement that may be used by patient 1280, through the use of communications system 1240, to communicate with medical professional 1282.

A diagnostic system 1274 may optionally be included in compartment 1202a. Diagnostic system 1274 may include mechanisms which enable diagnostic testing to be performed on patient 1280. Diagnostic system 1274 may include, but is not limited to including, an MRI machine, an x-ray machine, an ultrasound machine, an ECG/EKG machine, a radiation machine, a chemical test apparatus, and/or a thermometer.

Second compartment 1202b includes an administering mechanism 1276. Administering mechanism 1276 may generally be used to administer or to perform a medical procedure on patient 1280, e.g., to administer an injection such as a vaccine to patient 1280 and/or to obtain a biological sample such as a blood sample from patient 1280. Administering mechanism 1276 may include an apparatus such as a robotic arm or a movable platform which may facilitate enabling diagnostic system 1274 to be used on patient 1280. While administering mechanism 1276 and diagnostic system 1274 have been shown as being included in different compartments 1202a, 1202b, administering mechanism 1276 and diagnostic system 1274 may instead be included in the same compartment 1202a, 1202b.

It should be appreciated that in some embodiments, optional sanitizing arrangement 1244 may instead be, or may additionally be, included in first compartment 1202a. In addition, optional diagnostic system 1274 may be included in second compartment 1202b rather than in first compartment 1202b. That is, the allocation of optional sanitizing arrangement 1244 and diagnostic system 1274, as well as the allocation of telemedicine endpoint 1278 and administering mechanism 1276, may vary with respect to compartments 1202a, 1202b.

In one embodiment, medical professional 1282 may use a telemedicine endpoint 1284 to interact with vehicle 1201, e.g., to interact with telemedicine endpoint 1278 onboard vehicle 1201. Telemedicine endpoint 1284 may generally include, but is not limited to including, a display screen, a video camera, a microphone, a data entry arrangement such as a keyboard, a computing arrangement, and/or a communications system that enables telemedicine endpoint 1284 to communicate with communications system 1240 of vehicle 1201 over a network 1286. Network 1286 may be any suitable network including, but not limited to including, an LTE network, a 3G/4G/5G network, and/or a Wi-Fi network.

In general, medical professional 1282 may use telemedicine endpoint 1284 to communicate with patient 1280 when patient 1280 is in the vicinity of vehicle 1201, and is able to utilize telemedicine endpoint 1278 to remotely interact with medical professional 1282. For example, when patient 1280 is in vicinity of vehicle 1201, patient 1280 may interact with vehicle 1201 to gain access to telemedicine endpoint 1278 and, upon gaining access to telemedicine endpoint 1278, telemedicine endpoint 1278 may cooperate with telemedicine endpoint 1284 over network 1286 to establish communications. Telemedicine endpoint 1284 may generally include a face-to-face conferencing interface.

When administering mechanism 1276 is to be manipulated to facilitate treatment of patent 1280 or administering a medical procedure on patient 1280, administering mechanism 1276 may be controlled by medical professional 1282. By way of example, when administering mechanism 1276 is arranged to administer an injection to patient 1280, medical professional 1282 may remotely control administering mechanism 1276. A control arrangement 1288, which may include an interface which communicates with administering mechanism 1276 over network 1286 and using communications system 1240, may be used by medical professional 1282 to cause administering mechanism 1276 to take actions. Control arrangement 1288 may include hardware and/or software logic which facilitates the control of administering mechanism 1276, e.g., facilitates the control of a robotic arm and/or a mechanical platform. In one embodiment, medical professional 1282 may communicate with patient 1280 using telemedicine endpoints 1284, 1278 while remotely manipulating administering mechanism 1276 to substantially physically interact with patient 1280. In another embodiment, telemedicine endpoint 1278 includes an interface, as discussed above with respect to FIG. 7, which enables control arrangement 1288 to control administering mechanism 1276.

A vehicle used to support providing medical services such as vehicle 101 as shown in FIG. 7 and vehicle 1201 of FIG. 12 may be arranged to be configurable. For example, an apparatus that is carried in a compartment of a vehicle may be configured as a modular insert, or as a component that may be readily inserted in and/or removed from a compartment. By configuring diagnostics mechanisms, administering mechanisms, and telemedicine equipment as modular inserts which may be inserted into a compartment of a vehicle, a vehicle may be efficiently customized.

Figure 13:
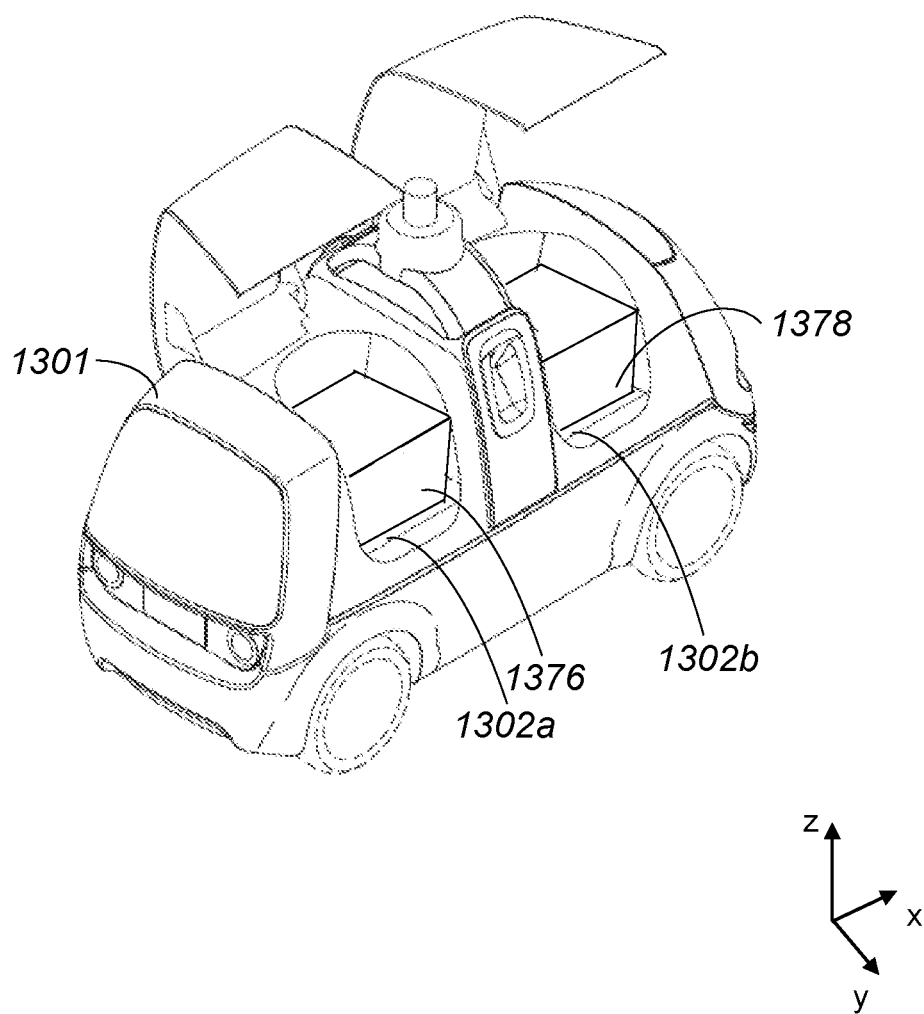
FIG. 13 is a diagrammatic representation of a vehicle with compartments which are arranged to receive modular inserts in accordance with an embodiment.

FIG. 13 is a diagrammatic representation of a vehicle with compartments which are arranged to receive modular inserts in accordance with an embodiment A vehicle, 1301, which may be an autonomous delivery vehicle, includes compartments 1302a, 1302b. Compartments 1302a, 1302b are arranged to carry modular inserts 1376, 1378, respectively. Modular inserts 1376, 1378 may generally include components configured to facilitate the use of medical 1301 to support medical uses, e.g., to provide medical treatment and/or to deliver goods associated with medical diagnoses and treatment. In one embodiment, modular insert 1376 may be an administering mechanism that is arranged to be used to execute or to provide a medical procedure to a patient, while modular insert 1378 may be a telemedicine interface or endpoint that is arranged to be used by a patient to communicate with a medical professional at a remote location.

Figure 14A:
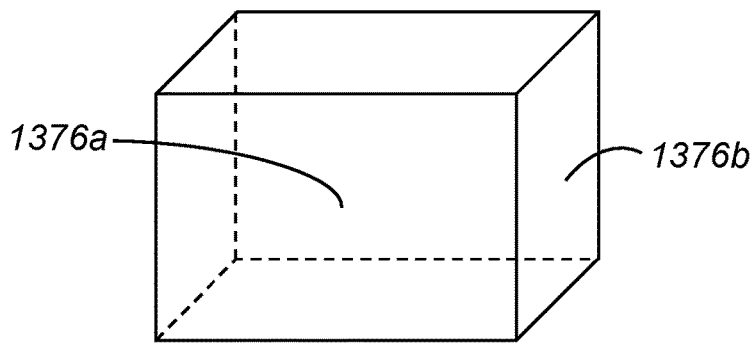
FIG. 14A is a diagrammatic representation of a modular insert, e.g., modular insert 1376 of FIG. 13, in accordance with an embodiment.
Figure 14B:
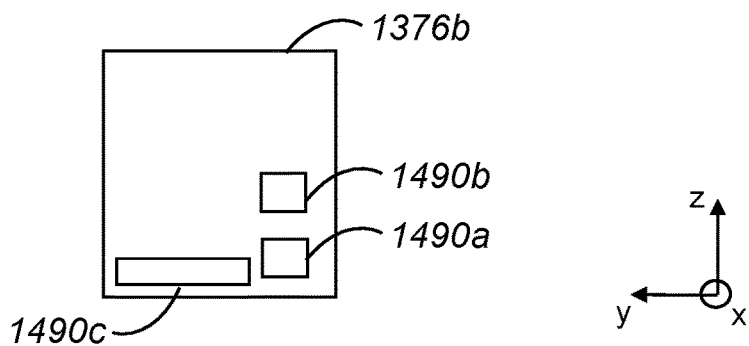
FIG. 14B is a diagrammatic representation of a side of a modular insert, e.g., side 1376b of FIG. 14A, in accordance with an embodiment.

Compartments 1302a, 1302b may generally include power interfaces, communications interfaces, and mechanical interfaces which are arranged to be coupled to modular inserts 1376, 1378, respectively. That is, to facilitate the insertion and removal of modular inserts 1376, 1378 into compartments 1302a, 1302b, respectively, modular inserts 1376, 1378 may include features which allow modular inserts 1376, 1378 to effectively be coupled to vehicle 1301, to draw power from vehicle 1301, and to communicate with vehicle 1301. With reference to FIGS. 14A and 14B, features of modular inserts 1376, 1378 which facilitate insertion and removal will be described in accordance with an embodiment. As shown in FIG. 14A, modular insert 1376 includes at least a first side 1376a and a second side 1376b. It should be appreciated that modular insert 1378 may generally include similar features as modular insert 1376.

In general, first side 1376a may be arranged to face out of compartment 1302a of FIG. 13 when compartment 1302a is open. Second side 1376b may include a power connector 1490a which is configured to draw power from vehicle 1301 of FIG. 13. Such power may be electrical power or battery power. It should be appreciated that if compartment insert 1376 includes a dedicated battery, power connector 1490a may be optional. Second side 1376b also includes a communications interface 1490b. Communications interface 1490b may be configured to support wired and/or wireless communications with vehicle 1301 of FIG. 13. For example, communications interface 1490b may be arranged to substantially connect to a communication bus on vehicle 1301 of FIG. 13, or communications interface 1490b may be arranged to engage in communications such as Bluetooth communications, Wi-Fi communications, LTE communications, and/or wireless 3G/4G/5G communications. Second side 1376b also includes a mechanical interface 1490c which is arranged to enable compartment insert 1376 to be mechanically coupled to compartment 1302a of FIG. 13.

Although only a few embodiments have been described in this disclosure, it should be understood that the disclosure may be embodied in many other specific forms without departing from the spirit or the scope of the present disclosure. By way of example, a vehicle with a compartment that includes the ability to disinfect, sanitize, sterilize, and/or clean items placed therein may be used for the capabilities of the compartment. For instance, a vehicle may be used at a field hospital or at a remote, e.g., outdoor, location at which medical procedures are performed to provide the ability to disinfect items such as medical tools. Similarly, a vehicle that carries components that may administer and/or run medical tests may be used at a field hospital or at a remote location at which medical procedures.

While the methods and systems described above have generally been described in the context of a shelter-in-place order or a stay-at-home order, it should be understood that the methods and systems are not limited to being utilized during a crisis such as a pandemic. By way of example, an autonomous vehicle as a mobile medical station may be used to provide medical testing, diagnostics, and/or treatment substantially anytime. In one embodiment, a mobile medical station may be deployed to rural communities to serve as a medical clinic.

The ability to disinfect or otherwise clean items transported by an autonomous vehicle is not limited to being used when there is a relatively high possibility that the items may be contaminated, e.g., with a virus such as COVID-19. In other words, transported items may be disinfected or otherwise cleaned whenever the items are onboard an autonomous vehicle with disinfecting or cleaning capabilities.

In some instances, it may be necessary to provide additional power capabilities on an autonomous vehicle. For example, it may be desirable to provide a dedicated power source to power optional sanitizing/cleaning system 344 of FIG. 3. Additional power may be provided by a power supply such as a battery pack located in a compartment of the autonomous vehicle.

The ability for an individual to access a compartment of a delivery vehicle in a contactless manner has been described as being achieved in some cases through communications with a fleet management system. In one embodiment, when a delivery vehicle is controlled via teleoperations, a remote operator may open a door on a compartment of the vehicle when the remote operator sees that a customer is ready to accept a delivery without departing from the spirit or the scope of the disclosure.

Specimens that may be obtained from a patient or a customer for testing may be any suitable specimen. Suitable specimens may include, but are not limited to including, skin cells such as those obtained from a cheek swab, hair, blood, saliva, phlegm, urine, stool, and teardrops. Substantially any liquids or solids associated with a human body may be collected as specimens for test purposes.

In one embodiment, when a telemedicine session is supported by a vehicle such as an autonomous vehicle, a medical professional participating in the telemedicine session may issue a prescription for a patient by writing a prescription which may then print out on a printer installed in a compartment on the vehicle. More generally, the medical professional may cause medical records to be provided to a patient using components carried on a vehicle. Such medical records may be provided using any suitable method including, but not limited to including, printing out the records, texting the records to a verified telephone number, emailing the records to a verified email address, etc.

The use of telecommunications equipment on a vehicle is not limited for use to support a telemedicine session. That is, a telepresence system on a vehicle may be used to support substantially any experience in which communications between a customer, e.g., a recipient of a service, and a service provider facilitates providing the customer with a service. Services may include, but are not limited to including, interactive experiences such as self-care experiences, beauty maintenance experiences, fitness training experiences, pet care experiences, and the like.

A medical professional may determine during a telemedicine session supported by an autonomous vehicle that a patient may need medication and, in lieu of providing a prescription for the medication, the medical professional may cause medication to be dispensed substantially directly to the patient using the autonomous vehicle. For instance, during a pandemic, medications that are anticipated to be needed by patients may be securely stored on an autonomous vehicle, and at the instruction of a medical professional, appropriate amounts of the medications may be dispensed to patients who test positive for a pathogen. It should be understood that common medications may generally be securely stored on an autonomous vehicle, and may be dispensed to patients as deemed appropriate by a medical professional.

A telemedicine system on a vehicle, e.g., telemedicine system 1278 of vehicle 1201 of FIG. 12, has been described as using a communications system of the vehicle to enable the telemedicine system to be used by a patient to interact with a medical professional. In one embodiment, a telemedicine system on a vehicle may have a dedicated communications system included in the telemedicine system.

When an autonomous vehicle provides medical services such as testing or vaccinations using equipment carried on the autonomous vehicle, the autonomous vehicle may provide a document, e.g., a certificate, which indicates that the testing has been performed, the results of the testing, the type of vaccines administered, etc. By way of example, if an autonomous vehicle is configured to provide testing for particular antibodies in the blood of a patient, the autonomous vehicle may cause a notification to be generated which indicates that the patient has the particular antibodies in his or her blood. Such a notification may be provided using any suitable method including, but not limited to including, printing out a document using a printer onboard the vehicle, texting the notification to a verified telephone number, emailing the notification to a verified email address, etc.

An autonomous vehicle may be arranged to accept donations of blood, and may carry equipment onboard that supports blood donations. For instance, an insert in a compartment of an autonomous vehicle may draw blood from a donor. In one embodiment, the insert may be configured to cause blood to be transfused from a donor substantially directly to a recipient. It should be appreciated that the insert may take a small sample of blood from a donor, and test the sample for suitability and to determine a blood type, before drawing blood from the donor for donation.

While an autonomous vehicle used to support medical uses has generally been described as either being used substantially with a medical professional via a teleoperations session, or without the involvement of a medical professional, such an autonomous vehicle may be used to support an on-site medical professional. For example, an autonomous vehicle may be used at a temporary location to provide equipment used by a medical professional who is physically present at the temporary location. Such an autonomous vehicle may generally serve as an autonomous mobile clinic.

As mentioned above, a disinfecting compartment of a vehicle may be used as an autoclave to provide disinfecting capabilities. Such disinfecting capabilities may be arranged to disinfect, for example, used medical-grade face masks to allow the masks to be safely reused.

As described above with respect to FIG. 9, a medical professional may order a test for a patient. In one embodiment, an autonomous vehicle may be dispatched to provide tests for substantially any customers who may wish to undergo a medical test or vaccination. For example, potential customers may be notified using any suitable means that an autonomous vehicle configured to provide a particular kind of test or to particular vaccine will be in an area at a certain time on a certain day. The potential customers may then decide whether to utilize the services provided by the autonomous vehicle.

In one embodiment, a customer or a patient may decide to request a test on a specimen, as for example a blood test on blood he or she provides. In such an embodiment, the customer or patient may drop off his or her specimen with an autonomous vehicle. The specimen may either be processed using equipment onboard the autonomous vehicle, or the autonomous vehicle may transport the specimen to a laboratory for testing. The tests to be run on the specimen may be specified by the customer or patient, or the tests to be run on the specimen may be determined by personnel at the laboratory upon receipt.

An autonomous vehicle has generally been described as a land vehicle, or a vehicle that is arranged to be propelled or conveyed on land. It should be appreciated that in some embodiments, an autonomous vehicle may be configured for water travel, hover travel, and or/air travel without departing from the spirit or the scope of the present disclosure.

The embodiments may be implemented as hardware, firmware, and/or software logic embodied in a tangible, i.e., non-transitory, medium that, when executed, is operable to perform the various methods and processes described above. That is, the logic may be embodied as physical arrangements, modules, or components. For example, the systems of an autonomous vehicle, as described above with respect to FIG. 3, may include hardware, firmware, and/or software embodied on a tangible medium. A tangible medium may be substantially any computer-readable medium that is capable of storing logic or computer program code which may be executed, e.g., by a processor or an overall computing system, to perform methods and functions associated with the embodiments. Such computer-readable mediums may include, but are not limited to including, physical storage and/or memory devices. Executable logic may include, but is not limited to including, code devices, computer program code, and/or executable computer commands or instructions.

It should be appreciated that a computer-readable medium, or a machine-readable medium, may include transitory embodiments and/or non-transitory embodiments, e.g., signals or signals embodied in carrier waves. That is, a computer-readable medium may be associated with non-transitory tangible media and transitory propagating signals.

The steps associated with the methods of the present disclosure may vary widely. Steps may be added, removed, altered, combined, and reordered without departing from the spirit of the scope of the present disclosure. For example, when a test equipment on a vehicle is used to administer a test, the test equipment may need the cooperation of a patient in order to successfully complete the test. In one embodiment, if a saliva sample is needed, the test equipment may manipulate a test tube such that the test tube is provided at a location in which a patient may easily spit into the test tube. Therefore, the present examples are to be considered as illustrative and not restrictive, and the examples are not to be limited to the details given herein, but may be modified within the scope of the appended claims.

What is claimed is:

1. A vehicle comprising:
    a chassis;
    a system, the system configured to cause the vehicle to operate autonomously, the system carried on the chassis, wherein the system is configured to cause the vehicle to drive autonomously from a second location to a first location;
    a first mechanism;
    a disinfecting system;
    a first compartment, the first compartment carried on the chassis, the first compartment having the first mechanism contained therein and the disinfecting system, the first mechanism configured to facilitate performing a first procedure, the disinfecting system configured to disinfect the first mechanism as the vehicle drives autonomously from the second location to the first location;
    a second mechanism, the second mechanism carried on the chassis, wherein the second mechanism is configured to support a telepresence session;
    a communications arrangement, the communications arrangement configured to obtain information from a fleet management system, the information arranged to indicate whether an individual is authorized to access the first compartment; and
    a contactless compartment access arrangement, the contactless compartment access arrangement including a sensor, the sensor being a motion sensor arranged to recognize a motion intended to cause the first compartment to become accessible to the individual when the information indicates that the individual is authorized to access the first compartment, the motion being an action taken by the individual, wherein the first compartment includes a door, the contactless compartment access arrangement being configured to enable the individual to access the first mechanism carried in the first compartment without physically contacting the door when the individual is authorized to access the first compartment, wherein the individual instructs the contactless compartment access arrangement to provide the access to the first mechanism using the sensor.

2. The vehicle of claim 1 wherein the first procedure is a first medical procedure, and wherein the first mechanism is configured to be remotely controlled to perform the first medical procedure.

3. The vehicle of claim 2 wherein the telepresence session is a telemedicine session and the second mechanism includes a face-to-face conferencing interface and a telemedicine interface, and wherein the telemedicine interface is configured to enable the first mechanism to be remotely controlled.

4. The vehicle of claim 3 wherein the face-to-face conferencing interface is configured to communicate wirelessly with a remote telemedicine endpoint during the telemedicine session, wherein the remote telemedicine endpoint is configured to remotely control the first mechanism to perform the first medical procedure on a patient at the first location.

5. The vehicle of claim 1 wherein the disinfecting system includes a sanitizing arrangement, the sanitizing arrangement configured to sanitize the first mechanism.

6. The vehicle of claim 1 further including:
    a second compartment, the second compartment carried on the chassis, the second compartment having the second mechanism contained therein.

7. The vehicle of claim 1 wherein the first procedure is a first medical procedure, and wherein the first medical procedure includes injecting a patient.

8. The vehicle of claim 1 wherein the first procedure is a first medical procedure, and wherein the first medical procedure includes obtaining a sample from a patient, the vehicle further including:
    a third mechanism, the third mechanism being arranged to process the sample as the vehicle autonomously departs from the first location.

9. A method comprising:
    autonomously driving an autonomous vehicle to a destination, the destination being associated with a patient, the autonomous vehicle including at least a first compartment, the first compartment having a first mechanism contained therein and a disinfecting system contained therein, the first mechanism configured to facilitate a first medical procedure, the disinfecting system configured to disinfect the first mechanism as the vehicle autonomously drives to the destination, wherein the at least first compartment includes at least a first door and a motion sensor, the motion sensor configured to recognize an action intended to cause the at least first door to open;
    verifying whether the patient is allowed to access the first compartment, wherein verifying whether the patient is allowed to access the first compartment includes verifying an identity of the patient, and wherein verifying the identity of the patient includes obtaining information from the patient and obtaining information from a fleet management system;
    at least temporarily preventing the patient from accessing the first compartment when it is not verified that the patient is allowed to access the first compartment;
    providing the patient with access to the first compartment when it is verified that the patient is allowed to access the first compartment and when the motion sensor recognizes the action intended to cause the at least first door to open performed by the patient, wherein providing the patient with access to the first compartment includes opening the at least first door and performing the first medical procedure on the patient using the first mechanism, wherein performing the first medical procedure on the patient using the first mechanism includes remotely manipulating the first mechanism; and
    supporting a telemedicine session using a second mechanism included in the vehicle, the second mechanism including a face-to-face conferencing interface and a telemedicine interface, the face-to-face conferencing interface configured to enable to the patient to participate in the telemedicine session with a remote party, and wherein the telemedicine interface is configured to enable the first mechanism to be remotely manipulated by the remote party.

10. The method of claim 9 wherein performing the first medical procedure on the patient using the first mechanism includes injecting the patient using the first mechanism.

11. The method of claim 9 wherein performing the first medical procedure on the patient using the first mechanism includes obtaining a sample from the patient using the first mechanism.

\* \* \* \* \*